US009518915B2

(12) United States Patent  
Friedersdorf et al.

(10) Patent No.: US 9,518,915 B2  
(45) Date of Patent: Dec. 13, 2016

(54) SENSING SYSTEMS AND METHODS FOR DETERMINING AND CLASSIFYING CORROSIVITY

(71) Applicant: LUNA INNOVATIONS INCORPORATED, Roanoke, VA (US)

(72) Inventors: Fritz John Friedersdorf, Earlysville, VA (US); Conrad Koenig Andrews, Charlottesville, VA (US); Jeffrey Coleman Demo, Charlottesville, VA (US); Mateja Putic, Charlottesville, VA (US)

(73) Assignee: Luna Innovations Incorporated, Roanoke, VA (US)

( * ) Notice: Subject to any disclaimer, the term of this patent is extended or adjusted under 35 U.S.C. 154(b) by 86 days.

(21) Appl. No.: 14/416,392

(22) PCT Filed: Jul. 15, 2013

(86) PCT No.: PCT/US2013/050424  
§ 371 (c)(1),  
(2) Date: Jan. 22, 2015

(87) PCT Pub. No.: WO2014/018288  
PCT Pub. Date: Jan. 30, 2014

(65) Prior Publication Data  
US 2015/0268152 A1 Sep. 24, 2015

Related U.S. Application Data

(60) Provisional application No. 61/675,996, filed on Jul. 26, 2012.

(51) Int. Cl.  
*G01N 7/14* (2006.01)  
*G01N 17/04* (2006.01)  
(Continued)

(52) U.S. Cl.  
CPC .............. *G01N 17/04* (2013.01); *G01N 19/10* (2013.01); *G01N 25/00* (2013.01); *G01N 27/02* (2013.01); *G01N 33/0031* (2013.01); *G01W 1/00* (2013.01)

(58) Field of Classification Search  
None  
See application file for complete search history.

(56) References Cited

U.S. PATENT DOCUMENTS

| 5,338,432 A | 8/1994 | Agarwala et al. |
| 6,623,616 B1 * | 9/2003 | Malver .................. G01N 17/00 204/404 |

(Continued)

OTHER PUBLICATIONS

International Preliminary Report on Patentability dated Feb. 5, 2015 in PCT/US2013/050424, 7 pages.

(Continued)

*Primary Examiner* — Andre Allen  
(74) *Attorney, Agent, or Firm* — Nixon & Vanderhye P.C.

(57) ABSTRACT

A corrosivity associated with each of multiple locations near, on, or within a structure exposed to an environment that can corrode the structure is determined. Each of multiple sensor nodes is mounted at a corresponding one of the locations and measures environmental sensor information using one or more environmental sensors and corrosion sensor information using one or more corrosion sensors. The environmental sensor information is processed to obtain for the sensing node a first atmospheric corrosivity category value in accordance with a corrosivity classification system, and the corrosion sensor information is processed to obtain a second atmospheric corrosivity category value for the sensing node in accordance with the corrosivity classification system. One or more of the first and second atmospheric corrosivity category values is provided for use in determining a corrosion classification value for each of the locations.

34 Claims, 14 Drawing Sheets

(51) Int. Cl.
  *G01N 19/10*  (2006.01)
  *G01N 25/00*  (2006.01)
  *G01N 27/02*  (2006.01)
  *G01N 33/00*  (2006.01)
  *G01W 1/00*  (2006.01)

(56) References Cited

U.S. PATENT DOCUMENTS

| | | | | |
|---|---|---|---|---|
| 6,952,095 | B1 | 10/2005 | Goldfine et al. | |
| 7,313,947 | B2 | 1/2008 | Harris et al. | |
| 8,085,165 | B2* | 12/2011 | Wavering | G01N 17/04 340/870.02 |
| 2008/0141780 | A1 | 6/2008 | Wavering et al. | |
| 2008/0204275 | A1 | 8/2008 | Wavering et al. | |
| 2011/0012628 | A1* | 1/2011 | Dobashi | G01N 17/02 324/700 |
| 2011/0210014 | A1* | 9/2011 | Garosshen | G01N 27/121 205/776.5 |
| 2012/0038377 | A1* | 2/2012 | Hamann | G01N 17/04 324/700 |
| 2013/0265064 | A1* | 10/2013 | Hamann | G01N 17/04 324/700 |
| 2016/0041085 | A1* | 2/2016 | England | G01N 17/043 436/6 |

OTHER PUBLICATIONS

R. Summitt et al, "PACER LIME: Part II—Experimental Determination of Environmental Corrosion Severity" Jun. 1980, at http://www.dtic.mil/docs/citations/ADA108552, 35 pages.
S. Morefield et al, "Development of Predictive Corrosion Model Using Locality-Specific Corrosion Indices" US Army Corps of Engineers, DoD Corrosion Prevention and Control Program, ERDC/CERL TR-09-22, Aug. 2009, 90 pages.
International Search Report for PCT/US2013/050424, mailed Oct. 14, 2013, 2 pages.
Demo, et al., "Wireless Corrosion Monitoring for Evaluation of Aircraft Structural Health", 2012 IEEE Aerospace Conference, pp. 1-10, (Mar. 10, 2012).
Demo et al., "Diagnostics and Prognostics for Aircraft Structures Using a Wireless Corrosion Monitoring Network", 2011 IEEE Aerospace Conference, pp. 1-10, (Mar. 12, 2011).
Demo et al., "Development of a Wireless Miniaturized Smart Sensor Network for Aircraft Corrosion Monitoring", 2010 IEEE Aerospace Conference, pp. 1-10, (Mar. 13, 2010).
I.S. Cole et al, "A Sensor-Based Learning Approach to Prognostics in Intelligent Vehicle Health Monitoring" *Materials Forum*, vol. 33, 2009, [in Proceedings of the 2nd Asia-Pacific workshop on structural health monitoring (2APWSHM), Melbourne, Dec. 2008] pp. 27-35.
Ivan S. Cole et al, "Development of a Sensor-Based Learning Approach to Prognostics in Intelligent Vehicle Health Monitoring" 2008 *International Conference on Prognostics and Health Management*, Oct. 6-9, 2008, 7 pages.

* cited by examiner

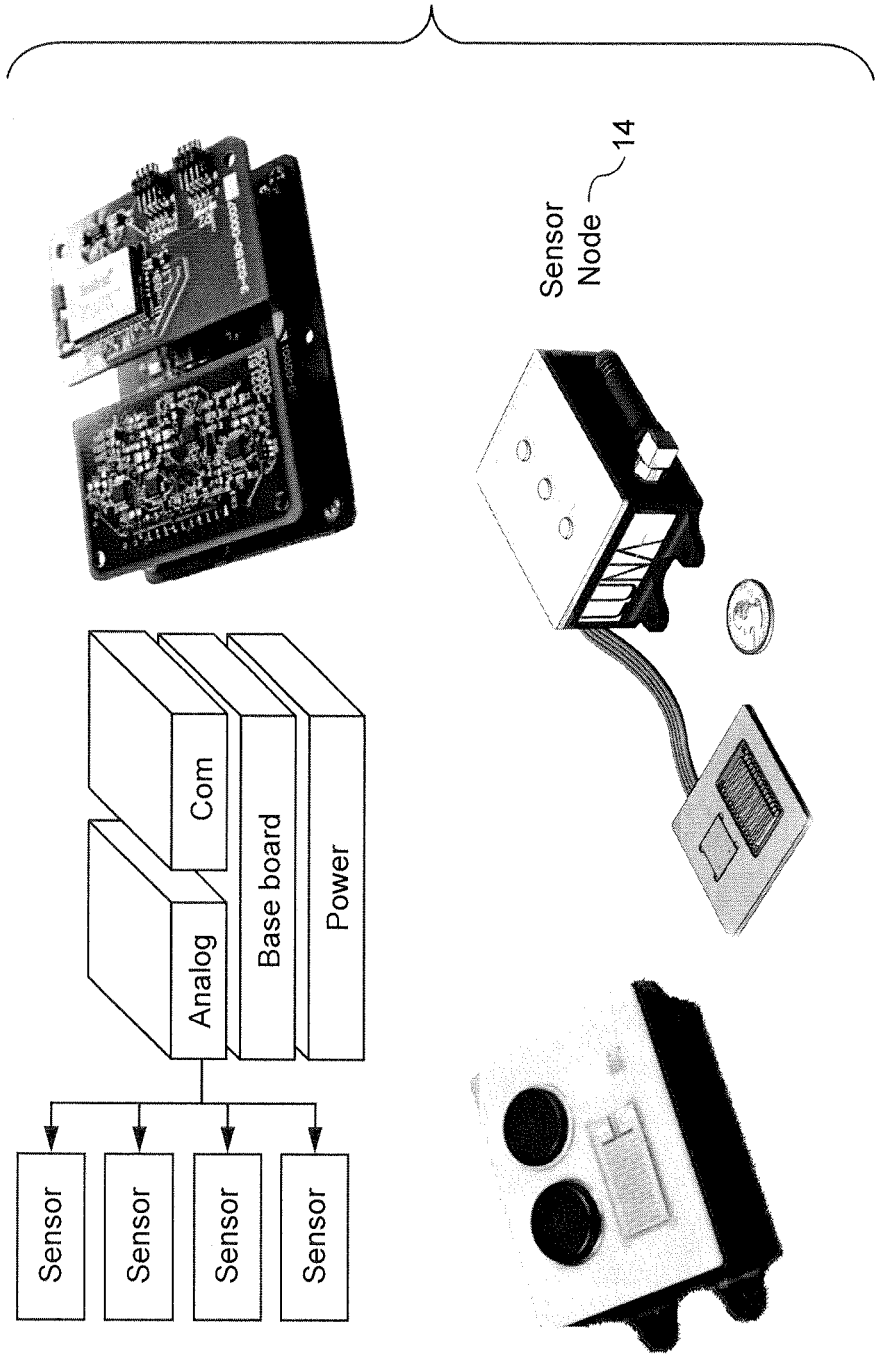

SENSING SYSTEMS AND METHODS FOR DETERMINING AND CLASSIFYING CORROSIVITY

PROVISIONAL APPLICATION

This application is the U.S. national phase of international Application No. PCT/US2013/050424, filed on Jul. 15, 2013, which designated the U.S. and claims priority from U.S. provisional patent application 61/675,996, filed on Jul. 26, 2012, the entire contents of each of which are incorporated herein by reference.

GOVERNMENT RIGHTS

This invention was made with Government support under Contract Nos. N68335-09-C-0099 and N68335-09-C-0107 awarded by the Department of the Navy. The Government has certain rights to the invention.

FIELD

The example embodiments described below relate to systems and methods for automatically detecting and classifying atmospheric corrosivity for different locations throughout a structure, e.g., a vehicle. A non-limiting example vehicle structure is an aircraft that may have been or can expected to be operated in corrosive environments, e.g., in or near marine environments.

BACKGROUND

The annual cost of corrosion to the US economy was estimated to be $276 billion in 2002. In many cases, industry manages corrosion based on predetermined schedules using past experience as a guide. Schedule based maintenance processes are expensive because inspections or maintenance needs to be very frequent to control risk adequately, and upset events or changing environmental conditions that cause corrosion are difficult to account for using schedule based processes. Visual observation of damage is the most widely used inspection practice for identifying corrosion, and this is ineffective in inaccessible areas and costly when disassembly is required. More sophisticated nondestructive evaluation (NDE) methods are useful for detecting the resulting damage to structures caused by corrosion. Once damage is detected, significant repair costs may be incurred to restore the structure or equipment. There are substantial societal benefits, economic, health, and safety related, to be gained by moving from schedule based processes to condition based practices for corrosion control in the fields of transportation, infrastructure, and manufacturing. The goal of achieving condition based maintenance for corrosion requires monitoring technologies that can measure environmental processes and corrosion to quantify severity. This corrosion monitoring system would allow for the anticipation of damage and the performance of inspection and maintenance based on actual corrosion severity.

Corrosion monitoring technologies for asset management depend on the availability of sensing elements and reliable models for characterizing corrosion. Known sensors directly measure corrosion damage to a structure, measure environmental conditions that cause corrosion, or measure corrosion to surrogate elements that can be used to make inferences about damage state.

A first category of sensors for direct corrosion damage measurements requires intimate contact with the structure. These sensors can be difficult to install and can become a point of failure at installation points. The sensors are usually point measurements or concentrated on a single component assembly, and this increases uncertainty about processes that occur in other adjacent components. Finally, these direct measurements only detect damage to the structure under test, and sometimes this damage may require significant repair when detected. There is a need to utilize sensors and corrosion characterization methods that are easy to install, have minimal risk of becoming points of damage initiation, have wider area coverage, and can detect corrosion or conditions that cause corrosion before substantial damage has occurred.

Known environmental sensors may be used to characterize corrosive environments and parameters including pollutant levels, rainfall totals, relative humidity, and temperature. Such characterizations may produce statistically significant results, but with usually weak correlation to the actual corrosion of structures in such an environment. Although these macro-scale atmospheric data can be applied using environmental models to predict the corrosion of structures and equipment at specific geographic locations, that prediction does not capture what are often the dominant local microclimate conditions around and within a structure that control corrosion affecting that structure. The use of environmental sensors near and within a structure can overcome some of these issues, but environmental models that use parameters, such as distance to the sea or total inches of rainfall, are typically not helpful for mobile structures or interior spaces of structures.

Another category of sensors that may be used to characterize corrosion for structure monitoring and management are surrogate sensing elements that react to environmental conditions. These surrogate corrosion sensors are used to make inferences about corrosion damage to the structure of interest. Surrogate corrosion sensors can be grouped as cumulative damage sensors and corrosion rate sensors. Cumulative damage sensors are based on electrical resistance (ER) measurements, where the resistance increases with the progression of corrosion. The sensitivity of ER sensors increases as the sensing element becomes thinner, but this significantly reduces sensor lifetime. Although an ER sensor may be designed to optimize both sensitivity to corrosion and sensor lifetime, high corrosion in a local area can still substantially reduce the ER sensor's longevity. Corrosion rate sensors are used to estimate the instantaneous rate of corrosion at any given time. These sensors may be used to detect galvanic currents or free corrosion rates of metals or alloys. Cumulative corrosion damage can be estimated with these sensors by integrating the periodic corrosion rate measurements over a given time period. The total corrosion, (corresponding to a total charge passed between the sensor electrodes), for a given period of time can be converted to a material mass loss using Faraday's Law. A history of the corrosion rate data is used to estimate cumulative corrosion damage. Both the cumulative corrosion and corrosion rate sensors measure the influence of localized microenvironment conditions, and as a result, sensor placement is key to producing an accurate measure for a given structure. Placement may be associated with importance of the structural elements or based on knowledge of conditions that produce the most significant corrosion risk.

Existing sensing technology and modeling approaches are inadequate to enable condition based maintenance for corrosion damage of high value assets. The inventor recognized there is a need for environmental sensors that can be easily located within or near a structure to produce data for a corrosion classification model that is based on relevant and accessible sensor data. There is also a need to combine the strengths of individual environmental and corrosion sensing methods in a multi-faceted sensor system that can leverage both environmental and corrosion sensors for atmospheric corrosivity classification to achieve reliable corrosion damage prediction of equipment and structures in various environments, e.g., different microclimates.

SUMMARY

A corrosivity associated with a location near, on, or within a structure exposed to an environment that can corrode the structure is determined. A sensor node is mounted at the location and measures environmental sensor information using one or more environmental sensors and corrosion sensor information using one or more corrosion sensors. The environmental sensor information includes one or more of measured relative humidity, air temperature, surface temperature and conductivity parameters, and the corrosion sensor information includes a corrosion rate parameter. The sensor node includes a computer processor that processes environmental sensor information to obtain for the sensing node a first atmospheric corrosivity category value in accordance with a corrosivity classification system, and processes the corrosion sensor information to obtain a second atmospheric corrosivity category value for the sensing node in accordance with the corrosivity classification system. One or more of the first and second atmospheric corrosivity category values are provided for use in determining a corrosion classification value for the location. An example corrosivity classification system may be based on an ISO 9223 corrosivity of atmospheres classification system.

Example corrosion sensors are disclosed. For example, one of the corrosion sensors includes electrodes made of the same metal, and wherein the corrosion rate parameter is determined from a current measured between the two metal electrodes. Another example corrosion sensor includes dissimilar metals, and wherein the corrosion rate parameter is determined from a galvanic current measured between the dissimilar metals. Yet another example corrosion sensor uses an eddy current induction sensor for measuring a total mass loss of a metal sample, and wherein the corrosion rate parameter is determined from the measured total mass loss of the metal sample and a time of exposure.

In example embodiments, the sensor node determines a chloride mass using conductivity measurements associated with the sensing node. For one example implementation, the chloride mass is determined only when a relative humidity detected at the sensor node is above 70% and the air temperature detected at the sensor node is lower than the surface temperature of the structure. A chloride deposition rate may also be determined knowing the time between measurements and change in chloride since the last measurement.

In example embodiments, the sensor node uses measured relative humidity, air temperature, and surface temperature to adjust the relative humidity based on the surface temperature of the structure.

In example embodiments, the sensor node determines a time of wetness associated with the sensing node. For example, time of wetness is determined based on an amount of time that the measured relative humidity exceeds a threshold value, or an amount of time that the measured conductivity exceeds a threshold value.

In example embodiments, the sensor node determines a corrosivity measurement error value or a corrosivity measurement confidence value using the environmental and the corrosion sensor information. An alert signal may be generated if the corrosivity measurement error value exceeds an error threshold or the corrosivity measurement confidence value is less than a confidence threshold. An alert signal may be generated to indicate a humidity sensor fault if the measured relative humidity is below a first threshold, the measured conductivity sensor exceeds a second threshold, and the corrosion rate parameter exceeds a third threshold. Moreover, an alert signal may be generated indicating a conductivity sensor fault if the measured conductivity is below a first threshold, the measured relative humidity exceeds a second threshold, and the corrosion rate parameter exceeds a third threshold. Moreover, an alert signal may be generated indicating a corrosion rate parameter fault if the measured corrosion rate is below a first threshold, the measured relative humidity exceeds a second threshold, and the conductivity sensor parameter exceeds a third threshold.

In example embodiments, the sensor node sends information regarding one or both of the first and second atmospheric corrosivity categories to one or more other nodes. The sensing node may communicate with the one or more other nodes via a wired interface or a wireless interface.

In example embodiments, the sensor node is battery powered or powered by external source. An external source may include power on board the structure and/or power from energy scavenging. Energy scavenging includes for example thermal, vibration, or solar scavenging techniques.

An example sensor node comprises one or more environmental sensors configured to provide environmental sensor information including one or more of measured relative humidity, air temperature, surface temperature, and conductivity parameters, and one or more corrosion sensors configured to provide corrosion sensor information including a corrosion rate parameter. The sensor node includes a data processor configured to process: (1) the environmental sensor information to obtain for the sensing node a first atmospheric corrosivity category value in accordance with a corrosivity classification system, and (2) the corrosion sensor information to obtain a second atmospheric corrosivity category value for the sensing node in accordance with the corrosivity classification system. A communications interface of the sensor node is configured to provide one or more of the first and second atmospheric corrosivity category values for use in determining a corrosion classification value for the location.

In example embodiments, the one or more environmental sensors include air temperature, surface temperature, and conductivity sensors, and the one or more corrosion sensors include a corrosion sensor with two identical metal electrodes and a corrosion sensor made of dissimilar metals.

In example embodiments, the one or more environmental sensors include an electrode sensor including two noble metal electrodes for estimating time of wetness and conductivity. As an example, the electrode sensor may include two interdigitated gold electrodes.

In example embodiments, the one or more environmental sensors include a conductivity sensor configured to be excited with a DC voltage or an AC voltage to obtain a conductivity measurement.

In example embodiments, the one or more corrosion rate sensors includes an electrode sensor composed of two electrodes of similar metal or alloy to estimate the corrosion rate. The electrode sensor may be configured to be excited with a DC voltage, stepped voltage, ramped voltage, or an AC voltage to obtain a corrosion rate measurement.

In example embodiments, the one or more corrosion rate sensors include an electrode sensor composed of two electrodes of dissimilar metal or alloy to estimate corrosion rate. The electrode sensor may include a zero resistance ammeter that measures galvanic current. The electrode sensor may include a resistor between the electrodes and a voltmeter to measure the voltage drop across the resistor to measure the galvanic current.

In example embodiments, the one or more corrosion sensors include an induction coil for making eddy current measurements of an alloy sample.

Another aspect provides a controller node for determining corrosivity associated with a structure exposed to an environment that can corrode the structure. The controller node includes a communications interface configured to receive from each of multiple sensing nodes associated with a corresponding location near, on, or within the structure measured environmental sensor information and measured corrosion sensor information. The environmental sensor information includes one or more of measured relative humidity, air temperature, surface temperature and conductivity parameters, and the corrosion sensor information includes a corrosion rate parameter. The controller node also includes a data processor configured to process: (1) the environmental sensor information to obtain for each of the sensing nodes a first atmospheric corrosivity category value in accordance with a corrosivity classification system, and (2) the corrosion sensor information to obtain a second atmospheric corrosivity category value for each of the sensing nodes in accordance with the corrosivity classification system. The data processor is also configured to provide one or more of the first and second atmospheric corrosivity category values for each of the sensing nodes for use in determining a corrosion value for the sensing node's corresponding location.

In example embodiments of the controller node, the data processor is configured to determine a mass loss rate associated with each sensing node, a chloride concentration associated with each sensing node, a time of wetness associated with each sensing node, and/or an error parameter associated with each of the sensing nodes that provides a confidence value associated with the determined corrosivity from that sensing node. The error parameter determined for each of the sensing nodes may be based on a comparison between the environmental sensor information and the corrosion sensor information received for that node.

BRIEF DESCRIPTION OF THE DRAWINGS

FIG. 4A is a diagram illustrating non-limiting examples of a sensor node;

DETAILED DESCRIPTION

Figure 1:
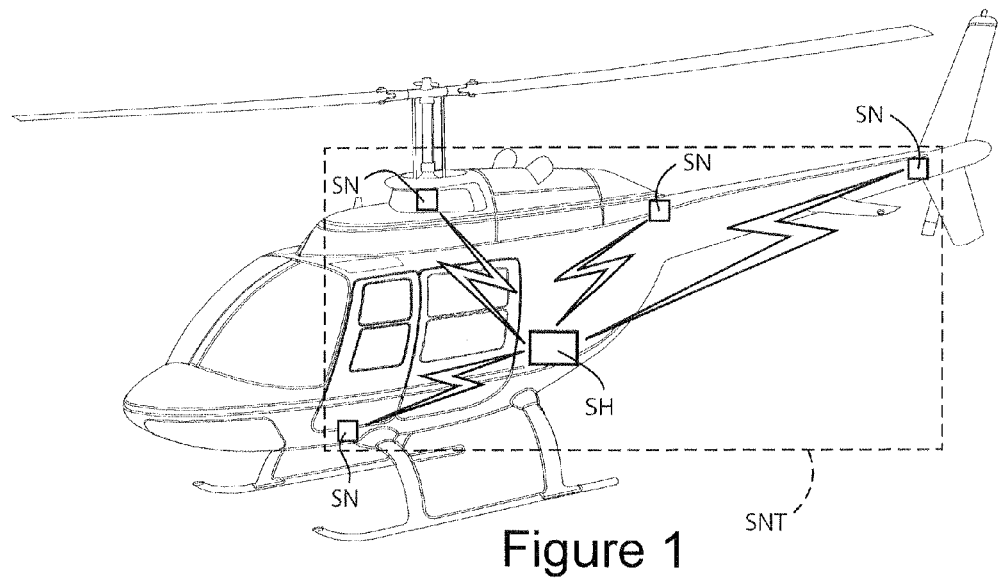
FIG. 1 is a perspective view of one implementation of a system according to an embodiment as disclosed herein associated with a rotary wing aircraft.

The following description sets forth example embodiments for purposes of explanation and not limitation. But it will be appreciated by those skilled in the art that other embodiments may be employed apart from these specific details. In some instances, detailed descriptions of well known methods, interfaces, circuits, and devices are omitted so as not obscure the description with unnecessary detail. Individual blocks are shown in some figures. Those skilled in the art will appreciate that the functions of those blocks may be implemented using individual hardware circuits, using software programs and data in conjunction with a suitably programmed digital microprocessor or general purpose computer, and/or using applications specific integrated circuitry (ASIC), and/or using one or more digital signal processors (DSPs). Software program instructions and data may be stored on a non-transitory, computer-readable storage medium, and when the instructions are executed by a computer or other suitable processor control, the computer or processor performs the functions associated with those instructions.

Thus, for example, it will be appreciated by those skilled in the art that diagrams herein can represent conceptual views of illustrative circuitry or other functional units. Similarly, it will be appreciated that any flow charts, state transition diagrams, pseudocode, and the like represent various processes which may be substantially represented in computer-readable medium and so executed by a computer or processor, whether or not such computer or processor is explicitly shown.

The functions of the various illustrated blocks may be provided through the use of hardware such as circuit hardware and/or hardware capable of executing software in the form of coded instructions stored on computer-readable medium. Thus, such functions and illustrated functional blocks are to be understood as being either hardware-implemented and/or computer-implemented, and thus machine-implemented.

In terms of hardware implementation, the functional blocks may include or encompass, without limitation, a digital signal processor (DSP) hardware, a reduced instruction set processor, hardware (e.g., digital or analog) circuitry including but not limited to application specific integrated circuit(s) (ASIC) and/or field programmable gate array(s) (FPGA(s)), and (where appropriate) state machines capable of performing such functions.

In terms of computer implementation, a computer is generally understood to comprise one or more processors or one or more controllers, and the terms computer, processor, and controller may be employed interchangeably. When provided by a computer, processor, or controller, the functions may be provided by a single dedicated computer or processor or controller, by a single shared computer or processor or controller, or by a plurality of individual computers or processors or controllers, some of which may be shared or distributed. Moreover, the term "processor" or "controller" also refers to other hardware capable of performing such functions and/or executing software, such as the example hardware recited above.

The technology relates to a sensor suite or system that may be used to measure corrosivity at multiple locations of a structure. FIG. 1 shows a non-limiting example structure corresponding to a helicopter aircraft AC. The AC is equipped with a sensing system which includes multiple sensor nodes SN at various predetermined locations on the airframe structure of the aircraft AC. The sensor nodes SN and sensor hub SH for a sensor network SNT where the sensor nodes SN communicate electronically with a sensor hub SH either directly or by hopping data to the sensor hub SH through the sensor network SNT. Preferably, the communication between the sensor nodes SN and sensor hub SH occurs wirelessly, but interconnection between the sensor nodes and hub SN, SH by wiring harnesses or other suitable communications media may be used. Although a rotary wing aircraft has been depicted in FIG. 1, the technology may be applied to fixed wing aircraft and to any other static or moveable structures where corrosivity monitoring is desired.

Figure 2A:
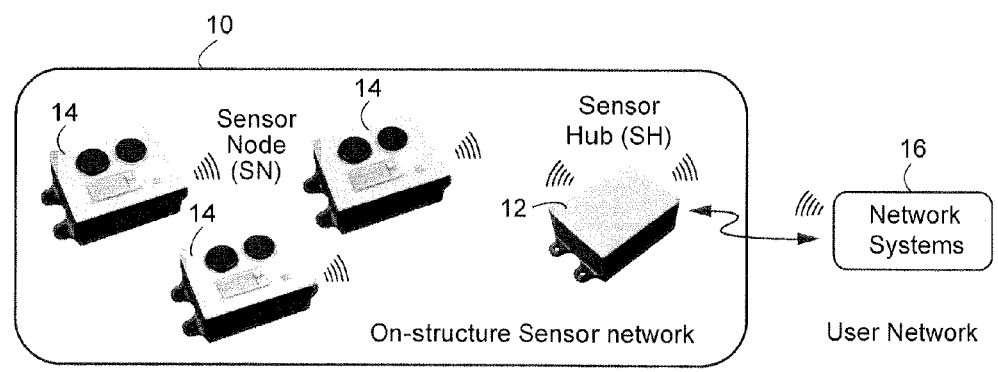
FIGS. 2A and 2B are diagrams illustrating a wireless sensor network and wired sensor network, respectively.

FIG. 2A shows an example on-structure sensor network 10 including multiple sensor nodes 14 placed on or near different locations of a structure to be monitored and a sensor hub 12. Each sensor node 14 includes a suite of sensors, examples of which are described below. The sensor hub SH may be designed to communicate via wired or wireless network communications with off-system network user devices such as a PC or laptop, or handheld devices for corrosivity data off-loading and/or presentation. Although one sensor hub 12 is shown, multiple sensor hubs may be used. The sensor nodes 14 and the sensor hub 12 communicate over a wireless interface. The sensor hub 12 may communicate, again wirelessly, if desired with one or more user networks and/or user devices 16 such as a PC or laptop, or handheld devices for corrosivity data off-loading and/or presentation. The network systems 16 may be on the structure as with an industrial process monitoring system or vehicle health usage monitoring system.

Figure 2B:
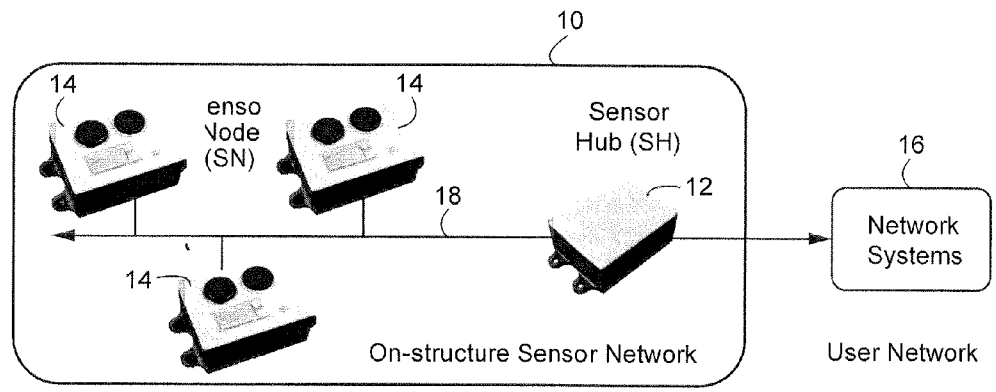

FIG. 2B shows another example on-structure sensor network 10 including multiple sensor nodes 14 placed on or near different locations of a structure to be monitored and a sensor hub 12. Although one sensor hub 12 is shown, multiple sensor hubs may be used. The sensor nodes 14 and the sensor hub 12 communicate over a wire interface. The sensor hub 12 may communicate, again over a wire interface, if desired with one or more user networks and/or user devices 16 such as a PC or laptop, or handheld devices for corrosivity data off-loading and/or presentation. The network systems 16 may be on the structure as with an industrial process monitoring system or vehicle health usage monitoring system.

The corrosion sensor system includes sensor nodes SN and a sensor hub SH for distributed monitoring of structures along with data processing functionality to convert sensor measurements into environmental corrosion severity classifications and estimates of cumulative corrosion. The corrosion sensor system detects conditions that cause corrosion and estimates corrosive severity and/or cumulative corrosion. The corrosion sensor system may, for example, employ a common hardware platform by incorporating low power electronics technologies with advanced embedded processing capabilities, functionality can be integrated at the transducer or application processor level, providing actionable notifications with no off-system processing required.

Once the corrosivity data has been transferred this corrosivity data can be stored in a user network database for long-term data trending. The sensor hub can also perform wired or wireless communications with the networked sensor nodes to consolidate the data. The sensor hub can perform power management for the sensor network and for energy scavenging devices (not shown) if desired. The system is preferably based on an open architecture with a configurable interface and loading options for a range of sensors. Sensor validation, data fusion, and/or diagnostic and prognostic algorithms can be embedded in the sensor hub and sensor node processors to improve reliability and power efficiency, and utility. The sensor hub processor can be used for data conversion and application functions and storing sensor data until it is retrieved by users or other nodes.

As one example, the sensor hub may be designed for wireless IEEE 802.15.4 data communications. But the modular design of the system also allows for wired connectivity, should that be desired. An advantage of wired connectivity between sensor nodes and sensor hubs is that if a sensor network SNT element such as a hub or node is located in an area where large amounts of ambient energy are available to an energy scavenging device, near a vibrating gearbox for example, the excess energy available at that location can be distributed to the rest of the sensor network SNT such as remote sensor nodes where reduced ambient energy is available. While this requires additional system wiring, it increases efficiency of the system by capturing and distributing available ambient energy.

Figure 3A:
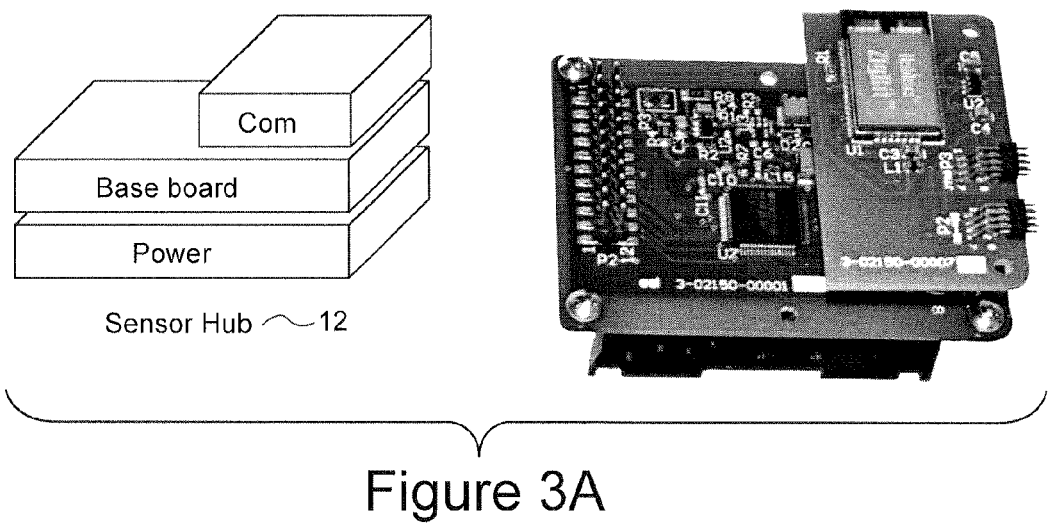
FIG. 3A is a diagram illustrating a non-limiting example of a controller node referred to as a sensor hub.
Figure 3B:
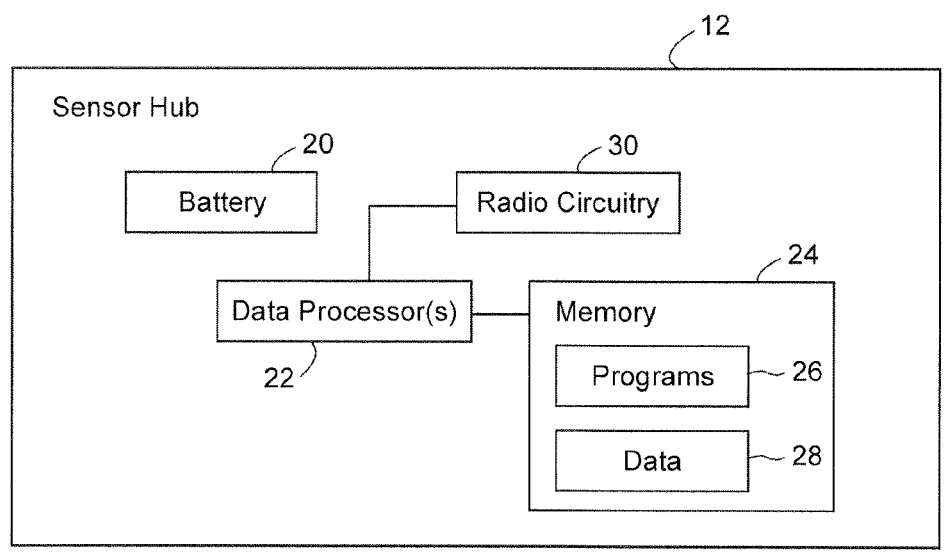
FIG. 3B is a function block diagram illustrating a non-limiting example of a controller node referred to as a sensor hub.

FIG. 3A shows a non-limiting example embodiment for a radio-based sensor hub 12 including a base board, a communications board, and a power board. FIG. 3B is a function block diagram for an example sensor hub and includes a battery power source 20 that powers one or more data processor(s) 22, memory 24, and radio circuitry 30. The battery 20 is preferably rechargeable to take advantage of energy scavenging, if available. The memory includes programs 26 and data 28 used by the one or more data processors 22 to perform the sensor hub functions such as those described.

FIG. 4A shows non-limiting example embodiments for a radio-based sensor node 14 including an analog board, a base board, a communications board, and a power board. The analog board connects to multiple sensors which may either be mounted on a surface of the sensor node (as shown in the bottom left portion of the figure) or coupled to the sensor node via wire (as shown in the bottom right portion of the figure) or other signal transport medium.

The base board incorporates two connectors: a first for the communications board and a second for the analog interface board. The first connector passes communications signals, such as a Serial Peripheral Interface (SPI) bus, and various universal asynchronous receiver/transmitter (UART) lines. Additionally, the first connector passes various digital I/O lines to the communications board that can be used as hardware interrupts to initiate wake-up events based on communications activities.

The analog interface connector provides access to a base board microcontroller via analog to digital converter pins, thus allowing for measurements to be made from various analog sensors. The connector also provides access to various digital I/O lines, and like the communications board interface, provides access to hardware interrupt lines. These external interrupt lines can be used to initiate wake-up events based on sensor outputs. In this regard, the analog interface may only be incorporated into the sensor node elements in the sensor hub—node architecture. In an example embodiment that uses common hardware for both sensor hub and node elements, the analog board interface on the base board may not be used in the sensor hub.

A variety of types of communications boards, depending on the type of communications used, may be employed in example embodiments. For wired communications between the sensor hub and a sensor node element, a pass through from the base board to the communications board could be sufficient, as hardware required for RS-485 communications may be incorporated on the base board. For wireless communications, hardware required to implement various wireless communications protocols may be provided on the communications board. For one example embodiment, a Meshnetics® ZigBit™ Zigbee® communications module may be included on the communications board, along with various power control circuits and a temperature sensing IC. The communications board is designed using a connector for attachment of an external antenna. This allows for tailoring of the antenna without modification to any other part of the system, should an external antenna be required.

The sensor node also includes an enclosure and a power source integrated to form a single unit that can be mounted at a location near, on, or within a structure for corrosion monitoring. The communications and base boards included in the sensor node device may be common components with the sensor hub. The analog interface board design, layout, and fabrication may be tailored to the specific set of sensors being supported.

Figure 4B:
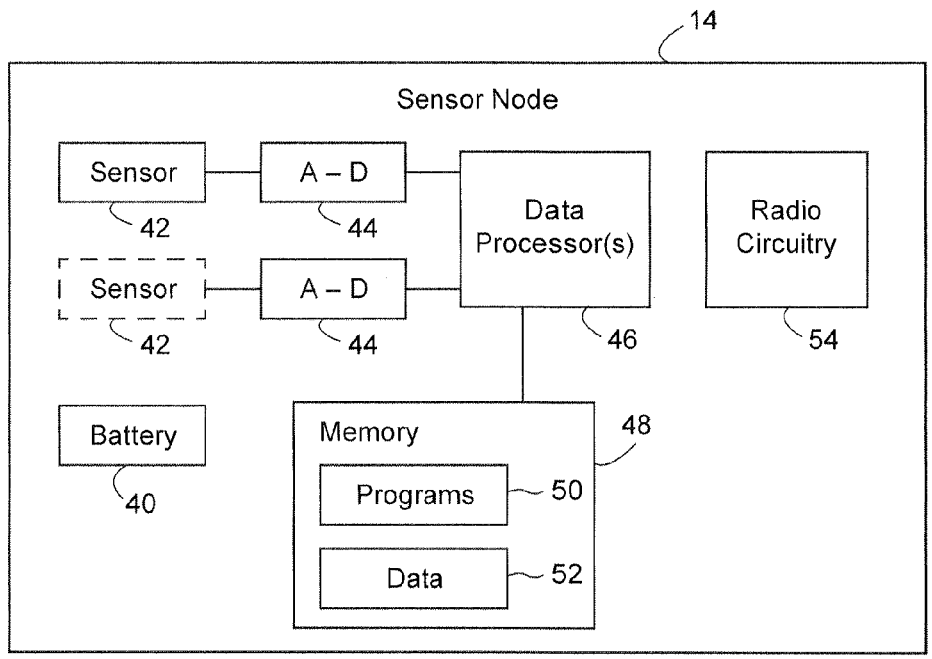
FIG. 4B is a diagram illustrating a non-limiting example of a sensor node.

FIG. 4B is a diagram illustrating a non-limiting example of a sensor node 14 and includes one or more sensors 42, corresponding analog-to-digital (A-D) converters 44 for converting analog signals provided by the sensors into digital signals, one or more data processor(s) 46 operatively connected to receive the digital sensor information from the A-D converters 44, memory 48, and radio circuitry 54. The memory 48 includes programs 50 and data 52 used by the one or more data processors 46 to perform various sensor node functions such as those described. A battery power source 40 powers the elements of the sensor node 14 including any sensor that needs external power to operate. The battery is preferably rechargeable to take advantage of energy scavenging and other charging opportunities, if available, without removal of the sensor node or hub or battery.

Figure 5A:
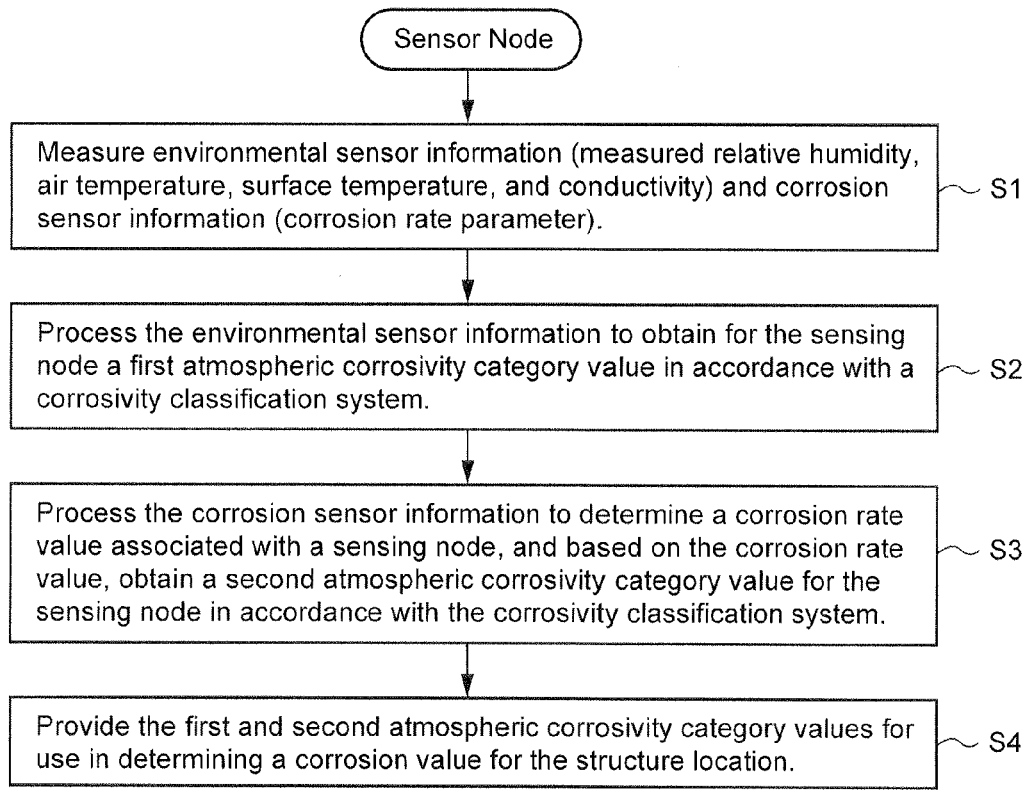
FIG. 5A is a flowchart illustrating example, non-limiting procedures that may be carried out by a sensor node.

FIG. 5A is a flowchart illustrating example, non-limiting procedures that may be carried out by a sensor node for determining corrosivity associated with a location near, on, or within of a structure exposed to an environment that can corrode the structure, where a sensor node is mounted at the location. The sensor node measures environmental sensor information using one or more environmental sensors and corrosion sensor information using one or more corrosion sensors (step S1). The environmental sensor information includes one or more of measured relative humidity, air temperature, surface temperature and conductivity parameters, and the corrosion sensor information includes a corrosion rate parameter. The environmental sensor information is processed to obtain for the sensing node a first atmospheric corrosivity category value in accordance with a corrosivity classification system (step S2). The corrosion sensor information is processed to obtain a second atmospheric corrosivity category value for the sensing node in accordance with the corrosivity classification system (step S3). One or more of the first and second atmospheric corrosivity category values is provided for use in determining a corrosion classification value for the location (step S4). The providing step may include sending information regarding one or both of the first and second atmospheric corrosivity categories to one or more other nodes such as the sensor hub 12 and/or another network or device.

Figure 5B:
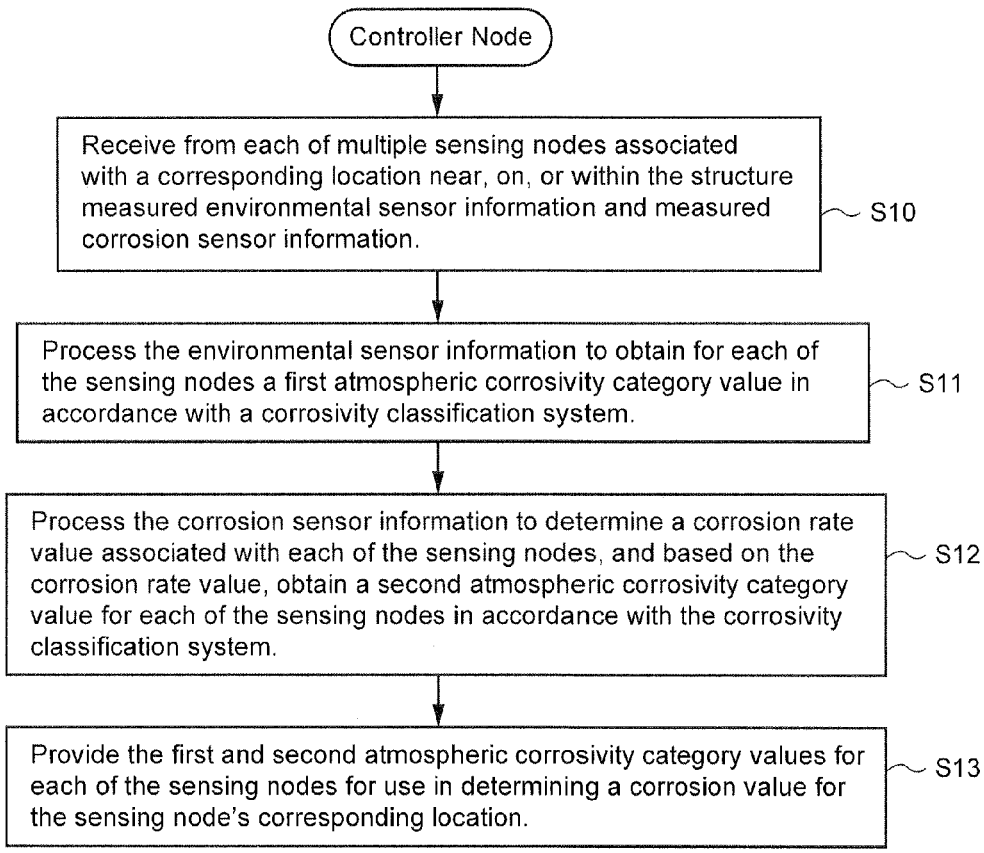
FIG. 5B is a flowchart illustrating example, non-limiting procedures that may be carried out by a controller node.

Although the example in FIG. 5A has much of the sensor data processing being performed locally at each sensor node, alternative example embodiments may have one or more controller nodes, such as but not limited to the sensor hub, performed some or all of the sensor data processing. FIG. 5B is a flowchart illustrating example, non-limiting procedures that may be carried out by a controller node for determining corrosivity associated with a structure exposed to an environment that can corrode the structure. The controller node receives from each of multiple sensing nodes associated with a corresponding location near, on, or within the structure measured environmental sensor information and measured corrosion sensor information (step S10). As above, the environmental sensor information includes one or more of measured relative humidity, air temperature, surface temperature and conductivity parameters, and the corrosion sensor information includes a corrosion rate parameter. The controller node processes the environmental sensor information to obtain for each of the sensing nodes a first atmospheric corrosivity category value in accordance with a corrosivity classification system (step S11) and processes the corrosion sensor information to obtain a second atmospheric corrosivity category value for each of the sensing nodes in accordance with the corrosivity classification system (step S12). The node then provides one or more of the first and second atmospheric corrosivity category values for each of the sensing nodes for use in determining a corrosion value for the sensing node's corresponding location (step S13).

The suite of sensors supported by the sensor node may include sensors for environmental parameters, corrosion rates, and cumulative corrosion damage that provide inputs that may be used to estimate environmental severity, condition of coatings and protection systems, and cumulative damage to specific alloys and structural components of the structure being monitored. Table 1 below describes various example sensors/monitors that may be employed.

TABLE 1

List of non-limiting example sensors useful for corrosion monitoring as part of the example sensor suite.

| Sensor | Measurand | Measurement Technique | Excitation | Output | Comment |
|---|---|---|---|---|---|
| Gold Interdigitated Electrodes (IDE) | Time of Wetness ($TOW_{Au}$) | High frequency impedance | 10 mV p-p AC - 100 kHz | Current $|Z_{hf}|$ | TOW based on $|Z_{hf}|$ threshold |
| | Solution Resistance ($R_s$) | High frequency impedance | 10 mV p-p AC - 100 kHz | Current $|Z_{hf}|$ | $R_s = |Z_{hf}|$ |
| Aluminum Alloy IDE | Polarization Resistance ($R_p$) | Low frequency impedance | 10 mV p-p AC - 0.5 Hz | Current $|Z_{lf}|$ | $R_p = |Z_{lf}|$ Corrosion inversely proportional to Rp |

TABLE 1-continued

List of non-limiting example sensors useful for
corrosion monitoring as part of the example sensor suite.

| Sensor | Measurand | Measurement Technique | Excitation | Output | Comment |
|---|---|---|---|---|---|
| Sacrificial Washer & Induction Coil | Corrosivity | Resonance circuit | 2.5 Vp-p 5.5 kHz 1.25 V DC | Vp-p | Voltage output increases with corrosion |
| Reference Induction Coil | Reference | Resonance circuit | 2.5 Vp-p 5.5 kHz 1.25 V DC | Vp-p | Gives a reference measurement for comparison |
| Humidity | Percent RH and Temperature | Digital Interface | Digital Interface | Digital Output | Air Temperature Relative Humidity |
| RTD Temperature | Temperature | Resistance | Current | V DC | Surface Temperature |
| Reference Electrode | Corrosion Potential | DC High impedance | None | V DC | Corrosion potential of aluminum alloy |
| Cu Electrical Resistance | Corrosivity | Resistance | — | Resistance | Increased resistance with corrosion |
| Cu/Al Galvanic Couple | Galvanic current | Zero resistance ammeter | DC current | Current | Galvanic current is measure of corrosion rate |

It is known that corrosion is dependent on meteorological conditions and natural occurring or pollutant chemicals. One or more environmental sensors that can be used to measure these atmospheric conditions include temperature, relative humidity, solution resistance, and electrochemical potential sensing elements.

Relative humidity (RH) and ambient air temperature ($T_a$) measurements may be made using, for example, a Sensirion SHT7x series commercial sensor, and surface temperature ($T_s$) measurements may be obtained with a standard thin film platinum RTD from US Sensor Corp. Direct measurements of component and operating environment temperatures are significant because of the Arrhenius temperature dependency of corrosion reaction rates. These temperature measurements may also be used for compensating other sensors and interface electronics that are susceptible to thermal drifts. Relative humidity provides an indication of the moisture content of the environment and when combined with surface and air temperature readings, provides a means to calculate the effective relative humidity ($RH_{eff}$) at the surface and dew point temperature (DP) for estimating time of wetness (TOW). Dew point is a valuable parameter, as it indicates when a film of water may be present on the surface of a metal, which is necessary for the occurrence of corrosion. Depending on salts and corrosion products on a surface, the surface may have moisture at humidities well below 100% or at temperatures above the dew point. Thresholds for determining wetness may take into account expected deliquescence and efflorescence of expected surface contaminants.

Figure 6A:
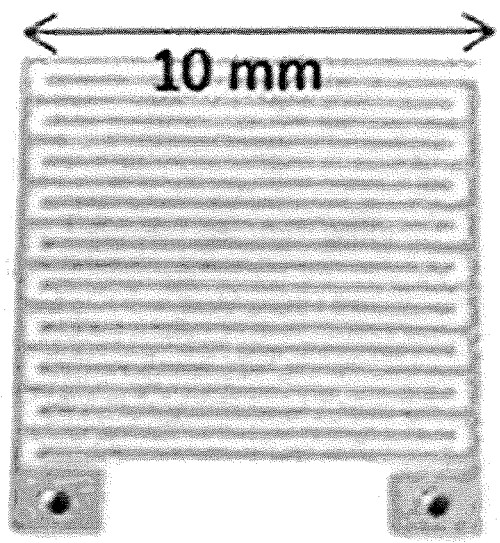
FIGS. 6A-6D are photographs depicting example environmental and corrosion sensors.

A noble metal (e.g., Au) interdigitated electrode (IDE) may also be included in the suite of sensors and provides a more direct measurement of time of wetness (TOW) and solution conductivity or solution resistance ($R_s$). An example is shown in FIG. 6A. Preferred excitation voltages are less than 100 mV and frequencies between 1 kHz to 500 kHz for the Au IDE sensors. At an appropriate frequency, (one example is 100 kHz), the $R_s$ measurement is independent of electrolyte salt species, and strongly dependent on the solution conductivity. For high chloride or marine environments, the solution resistance, measured with a Au IDE sensor, may be used to estimate chloride mass accumulation rate ($\dot{m}^{Cl}$).

Figure 6B:
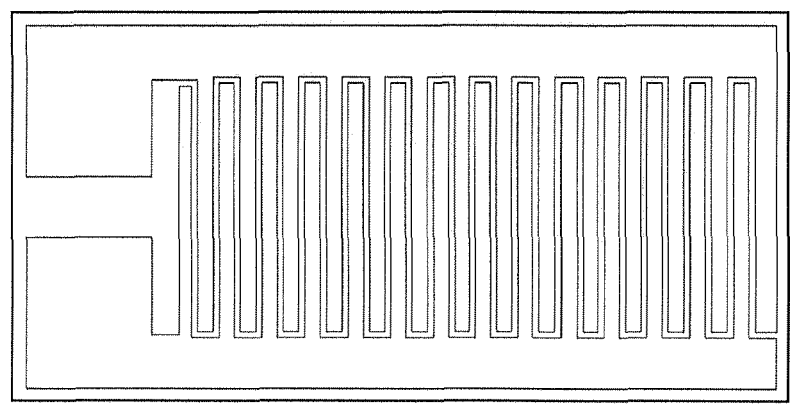
Figure 6C:
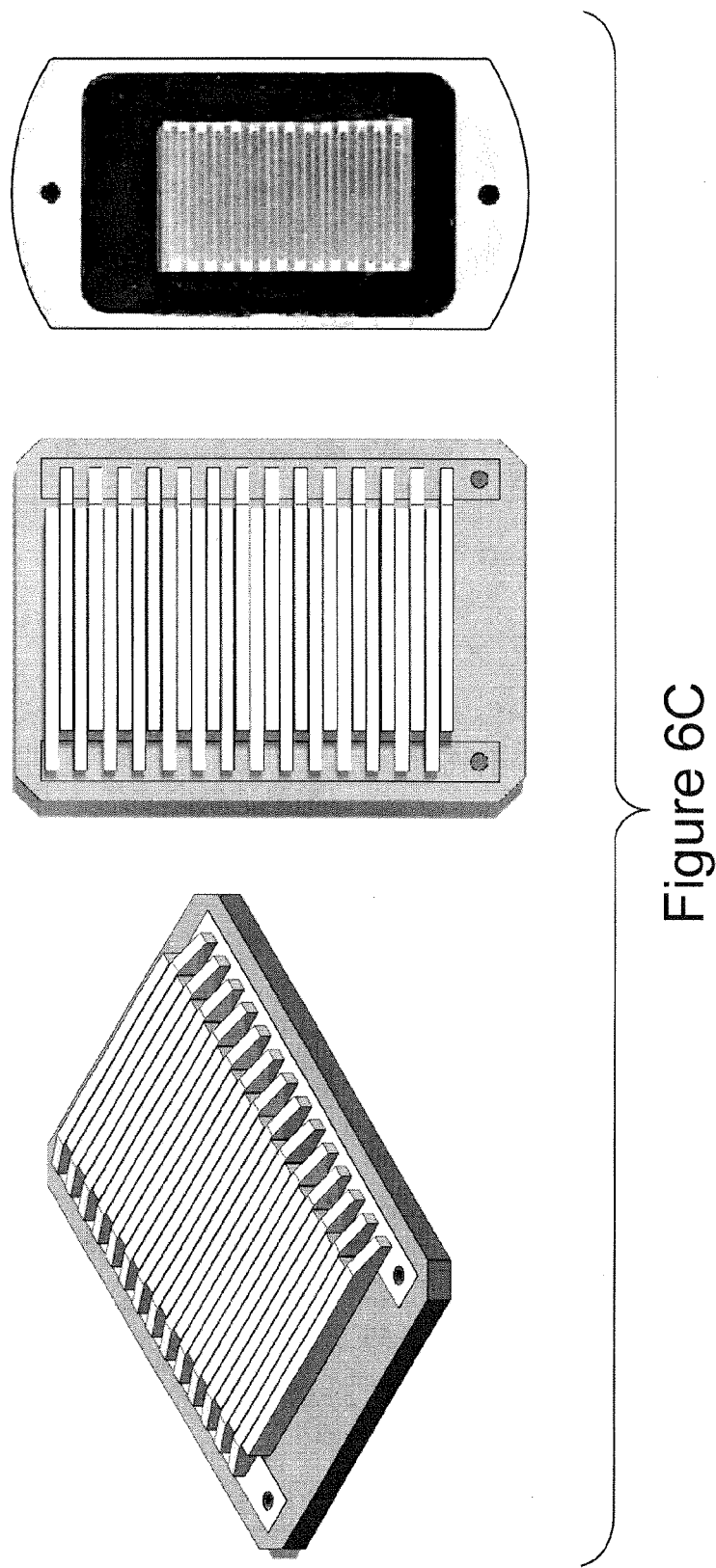
Figure 6D:
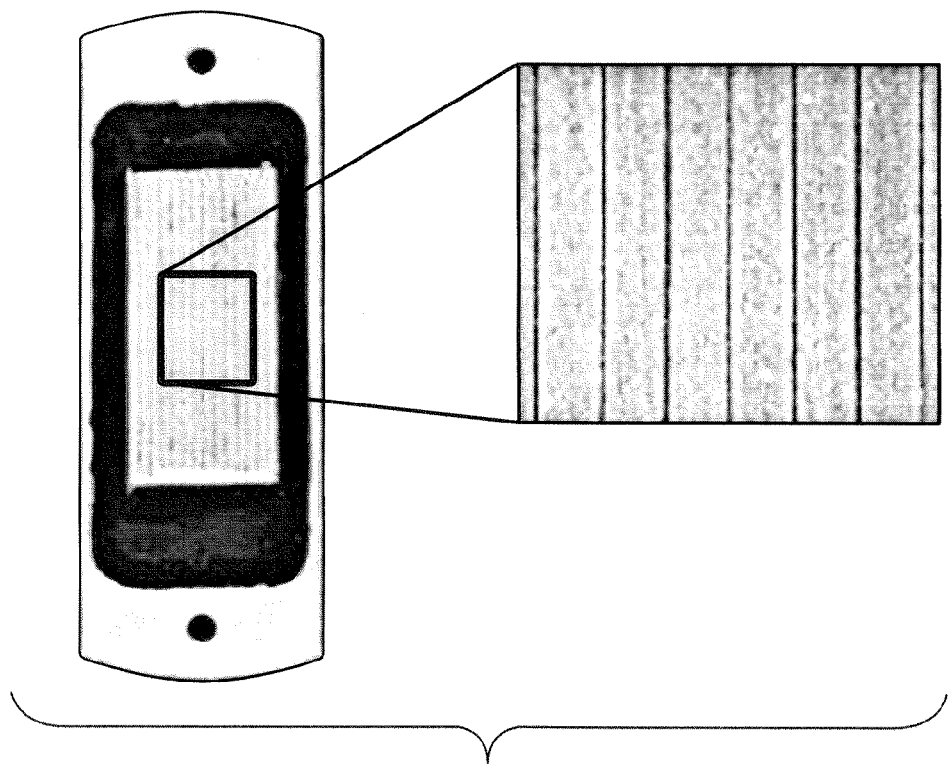

Corrosion rate measurements can be made with a variety of corrosion sensors to obtain measurements of cumulative corrosion, free corrosion rate, and galvanic corrosion rate. Cumulative corrosion sensors include metal resistance or inductive eddy current measurement devices to quantify mass loss. One example type of corrosion rate sensors includes IDEs for measuring corrosion rate ($i_{corr}$), such as that shown in FIG. 6B. The IDE in FIG. 6B may be fabricated by patterning a thin metal or alloy sheet using vapor deposition, etching and lithographic techniques, or methods as described in USPA 20070173048. FIG. 6C shows an IDE fabricated by stacking metal of alloy sheets. The IDE type corrosion sensors estimate the free corrosion or open circuit corrosion rate using impedance measurements. These types of impedance measurements are used to obtain the polarization or charge transfer resistance of an electrode. Another example type of corrosion rate sensors includes bimetallic galvanic couples for measuring galvanic current ($i_g$). FIG. 6D shows an example of this type fabricated by stacking two different alloy or metal sheets to form a bimetallic IDE used to measure the galvanic corrosion between the two dissimilar alloys or metals.

Measurements of corrosion rate can be made using a variety of sensor types and electrode configurations. Electrochemical methods may utilize either three electrodes or two electrodes to make rate measurements. These sensors can be used to estimate the free corrosion or open circuit corrosion rate by determining the circuit impedance using low amplitude voltage excitation of 100 mV or less at frequencies of 10 Hz or less. In the case of two electrode measurements, two alloy electrodes are used to obtain corrosion rate measurements using traditional techniques of linear polarization resistance or electrochemical impedance spectroscopy (EIS) to obtain polarization resistance ($R_p$) measurements. Assuming a value for the Stern-Geary constant ($\beta$), the corrosion rate ($i_{corr}$) can be calculated using the Stern-Geary equation:

$$R_p = \frac{\beta}{I_{corr}}; \text{ or } i_{corr} = \frac{\beta}{R_p * A} \tag{1}$$

where $I_{corr}$ is the measured current, and A is the electrode area.

$$\beta = \frac{b_a b_c}{2.3(b_a + b_c)} \quad (2)$$

where $b_a$ and $b_c$ are the anodic and cathodic Tafel slopes.

$$Z_{\omega \to 0} = 2R_p + R_s, \text{ and } Z_{\omega \to \infty} = R_s \quad (3)$$

$$R_p = \frac{Z_{\omega \to 0} - R_s}{2}; \text{ or } R_p = \frac{Z_{\omega \to 0}}{2} \quad (4)$$

Two electrode measurements can be made for any alloy of interest such as steel or aluminum that is configured into a parallel plate or interdigitated electrodes (IDEs). From time based measurements of corrosion rate, the cumulative corrosion is obtained using Faraday's Law (Equation 10) and integrating the mass loss rates (MR) over a given exposure time.

$$MR = \frac{i_{corr}}{F} \frac{MW}{z} \quad (5)$$

where MW is the molar mass of the alloy, z is the valence of ionic species produced by corrosion, and F is Faraday's constant.

Bimetallic galvanic corrosion sensors can be formed from any combination of dissimilar metals and alloys. These are typically chosen based on the alloys being used in the structure of interest. The two dissimilar metals form a galvanic couple, the current between the two being dependent on the environment and difference in electronegativity and reaction kinetics of each electrode. Sensor assemblies can utilize zero resistance ammeters with three electrode (with reference electrode) and two electrode geometries. The two electrode configuration for measuring galvanic current is the most useful for this sensing application. The electrode geometry can be a simple parallel plate design or a more complex interdigitated electrode. In either case, the total area of each electrode can be varied based on the application or desire to rate limit the galvanic corrosion processes on either the anodic or cathodic reactions. The separation distance can be varied to simulate specific component geometry or achieve different degrees of sensitivity to environmental conditions. The measured galvanic current ($i_g$) densities (based on the anode area) can be used like $i_{cur}$ in Equation 5 to determine the mass loss rate, and the cumulative corrosion damage is calculated by integrating the rate for a given time period.

Figure 7:
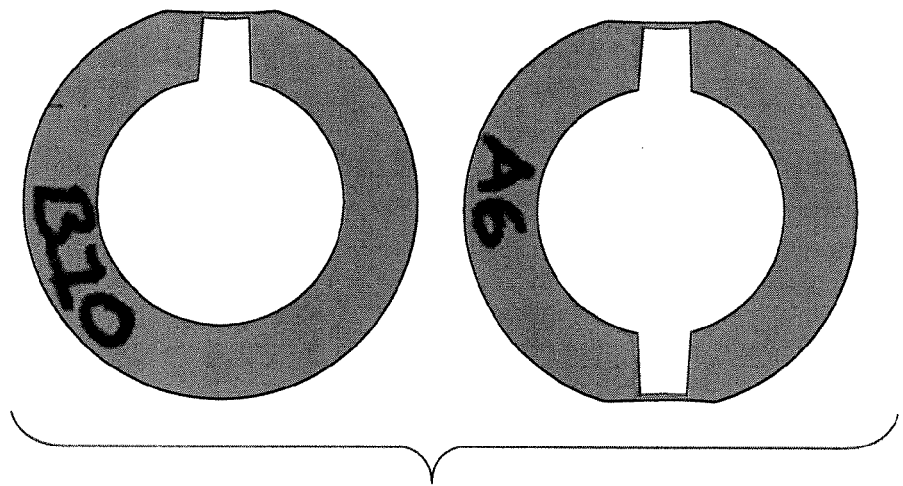
FIG. 7 is a photograph showing aluminum alloy washers that may be used as inductive corrosion sensors.

Many non-destructive evaluation (NDE) applications use eddy current techniques that operate on the principle of measuring inductance of a coil probe in the presence of material sample. The inductive corrosion sensor is composed of a sacrificial sample of the alloy of interest that is permanently coupled with an inductive eddy current probe to quantify corrosion damage. The probe induces eddy currents in the sample material, which generate predictable changes in magnitude and phase as material is lost from the sample. These changes affect the electrical load on the probe and in turn, alter its impedance. The inductive corrosion sensors utilize a flat washer sample of any alloy of interest, such as aluminum alloys. FIG. 7 is a photograph showing example aluminum alloy washers that may be used as inductive corrosion sensors. Depending of the corrosion process the washers may have gage sections that are oriented relative to the rolling direction to promote a specific corrosion mechanism such as intergranular or exfoliation corrosion. A protective coating can be used to mask all but the gage areas of the sample material.

The suite of sensors described above provides comprehensive information regarding corrosion and environmental severity. The service life of a component depends on the level of use. In terms of corrosion, use can be defined by the historical environmental exposure. A suite of sensors selected specifically to provide information on environmental severity, corrosion rate, and cumulative corrosion damage can be used to predict damage of a component or structure, or determine appropriate inspection and maintenance intervals based on level of corrosion use. The local micro-environment surrounding a component is continuously quantified with temperature, relative humidity, time of wetness, and solution conductivity measurements. By coupling the environmental conditions that promote corrosion with the actual material corrosion measurements of the inductive, corrosion rate or galvanic corrosion sensors, estimates of likelihood of occurrence and severity of corrosion can be made. This information is valuable in that it may reduce the need to inspect difficult to access areas, allow for more rapid remediation, and serve to predict future damage states based on projections of historical trends.

Both environmental severity and measurements from standard materials can be used to classify corrosivity and predict corrosion rates. For example, the Battelle model uses percent of time above certain humidity values, along with precipitation totals, and chloride deposition; while, the ISO standards are based on time of wetness (RH>80% and temperature >0° C.), and $SO_2$ and chloride deposition rates. The sensor suite has the capacity to obtain RH and TOW data for direct use in these standard models, and in marine environments chloride species (NaCl) can be determined from $R_s$ to obtain chloride deposition rates. The ISO method supports determination of corrosivity for a range of alloys and is applicable to sheltered spaces. The sensor suite would also be compatible with the Battelle model when the data are combined with local total rainfall amounts. The ISO method is preferred for autonomous operation and embedding within the sensor network system.

One non-limiting example way to objectively classify corrosivity of atmospheres is based on ISO 9223 which uses both alloy corrosion and environmental parameters. By combining corrosion sensors and environmental sensors in a sensing system that employs multiple different types of sensors, the local corrosivity of atmosphere can be characterized for local microclimates around and within a structure. A high degree of accuracy and reliability in terms of determining such local corrosivity is achievable using objective classifications based on environmental and corrosion rate data. Table 2 below gives the ISO classification of corrosivity based on aluminum corrosion rates that can be measured with the sensor suite. Similarly, ISO also provides a means to use sensor suite environmental parameters to estimate the corrosivity categories of Table 2. Regardless of whether corrosion rate or environmental data are used, the classification serves as an easily recognized measure of severity that can be used to adjust inspection and maintenance intervals or anticipate level of damage to a structure.

TABLE 2

Corrosivity categories for aluminum according to ISO 9223.

| | Corrosivity Category | | | | |
|---|---|---|---|---|---|
| | C1 | C2 | C3 | C4 | C5 |
| | Very Low | Low | Medium | High | Very High |
| Corrosivity Al Corrosion (g/m² * a) | Negligible | $r_{corr} \leq 0.6$ | $0.6 < r_{corr} \leq 2$ | $2 < r_{corr} \leq 5$ | $5 < r_{corr} \leq 10$ |

The sensor suite data is sampled at rates appropriate for corrosion processes ranging from minutes to tens of minutes. The channels of data being recorded at every time interval may include the environmental and corrosion measurements given in Table 2 above. The system provides for substantial data reduction and sensor validation at the node. ISO classification is accomplished with environmental and corrosion measurements using both total exposure time and user selectable intervals. This approach supports the determination of overall severity for the service life of the component or structure of interest, and identification of shorter duration corrosion events.

The total exposure time classification data are preserved over the full life of the corrosion sensor node, and can be input to new nodes to give continuity for monitoring of the complete life of a structure. The raw data used to obtain interval classification data are typically preserved only for the time between inspections. The system can provide event alarms based on environmental and corrosion rate classification data. If an alarm occurs the raw data will be available for downloading at the time of inspection. If no alarm is recorded, the data will not be retained or transmitted to the user, unless a user initiates a request for the raw interval data. Automated sensor validation tests may be executed each time samples are collected, and recurring deviations from expected values will be used to establish sensor faults.

Corrosion classification is accomplished by measuring mass loss from standard specimens of aluminum or steel after one year of exposure [ISO 9226]. Mass loss data is converted to corrosion rates given as grams lost per square meter annually (g/(m²*a)) (Table). The corrosivity categories can be determined from the corrosion rate sensors or galvanic sensors described above using Equation 5 and converting to the proper units. Specifically, the sensor suite can be used to measure the polarization resistance ($R_p$) of an IDE sensor of aluminum periodically for a given time interval ($\Delta t$). The polarization resistance is converted to a corrosion rate using Equation 1 and the mass loss rate for the interval ($MR_n$) is calculated from Equation 5. The mass loss rate for a given time period (MR) may then be determined by dividing the mass loss during the preceding time period and the present interval by the total time period of interest ($t_{n-1}$ and $\Delta t$).

Figure 8:
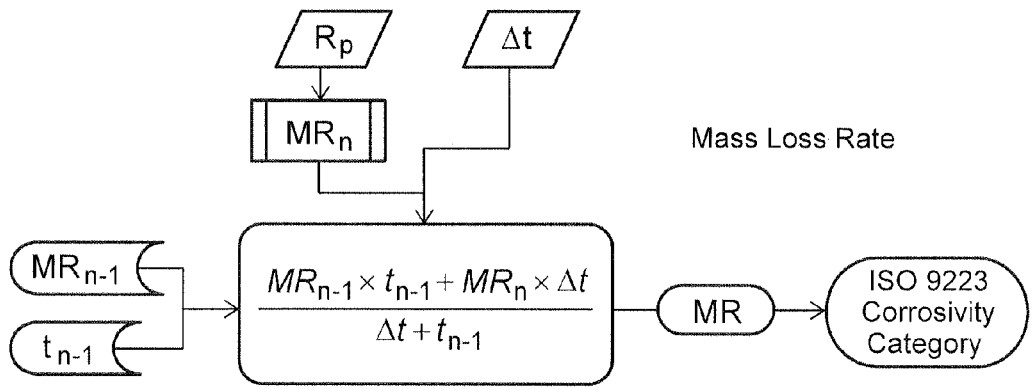
FIG. 8 is a flow chart showing non-limiting example procedures for transforming raw corrosion rate (Al IDE) sensor data into ISO 9223 corrosivity categories.

FIG. 8 is a flow chart showing non-limiting example procedures for transforming raw corrosion rate (Al IDE) sensor data into ISO 9223 corrosivity categories over a number of time intervals (n). The polarization resistance $R_p$ is converted to a mass loss rate $MR_n$ for the current time interval $\Delta t$. Using stored values for the previous total average mass loss rate $MR_{n-1}$ and the total prior exposure time $t_{n-1}$, the new total mass loss rate MR can be calculated in accordance with the formula shown in the center block of the flow chart. The new mass loss rate MR is used to establish the corrosivity category according to ISO 9223.

Figure 9:
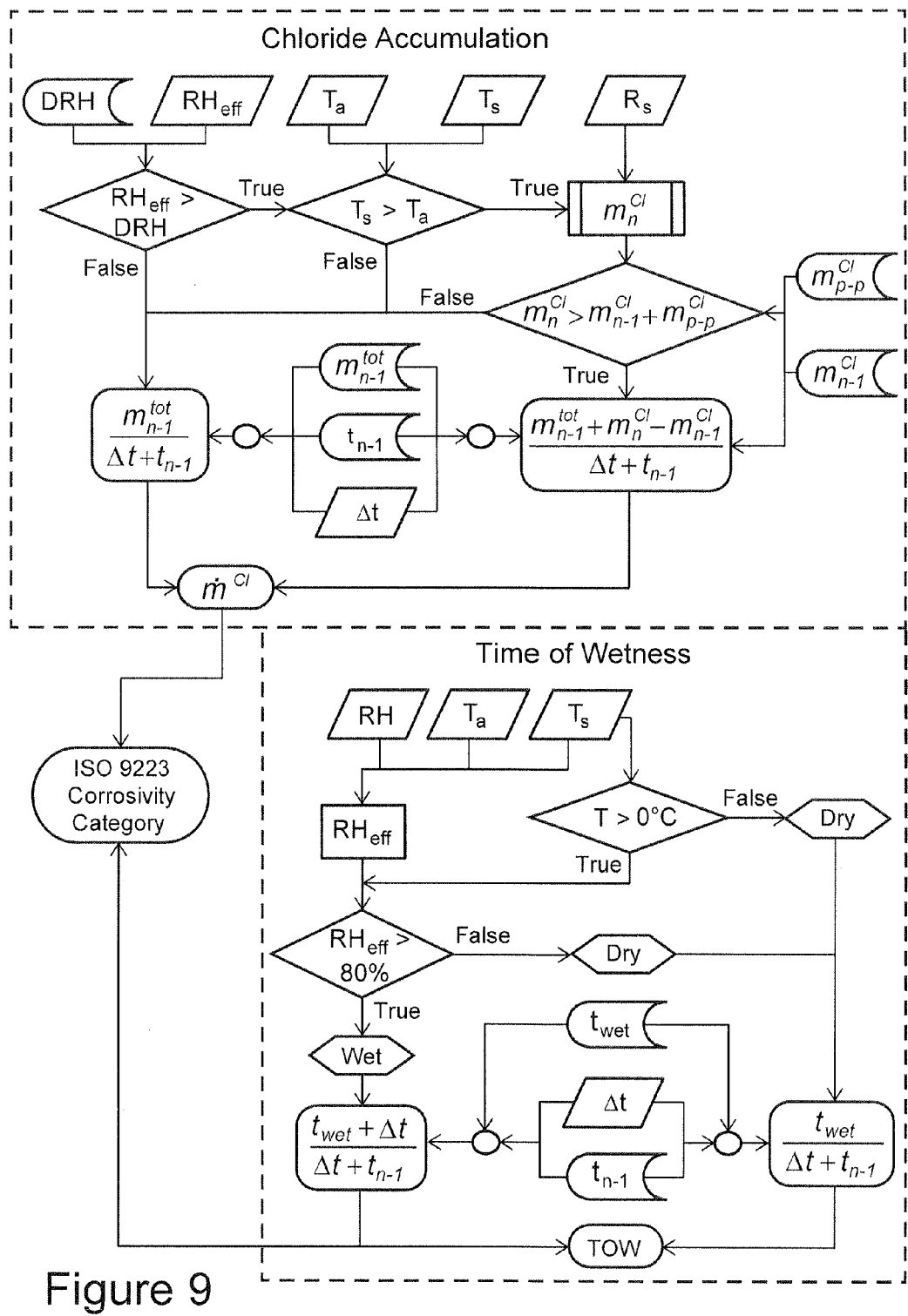
FIG. 9 is a flow chart showing non-limiting example procedures for transforming raw relative humidity and solution resistance (Au IDE) sensor data into ISO 9223 corrosivity categories.

FIG. 9 is a flow chart showing non-limiting example procedures for transforming raw relative humidity and solution resistance (Au IDE) sensor data into ISO 9223 corrosivity categories. Corrosion categories can also be determined by environmental measurements of time of wetness (TOW) and pollution levels or air-borne salinity. The relative humidity data is used to calculate the ISO time of wetness by summing the time RH or effective relative humidity ($RH_{eff}$) is greater than 80% and dividing by the total exposure time as shown in Table 3 below. An example embodiment for determining TOW uses the RH, air temperature, and surface temperature measurement. This embodiment is advantageous when significant temperature differences exist between the structure and air temperature. Using RH, air temperature, and surface temperature, the effective relative humidity $RH_{eff}$ can be calculated using known methods. If the surface temperature $T_s$ is less than 0° C., or the $RH_{eff}$ is less than 80%, then the surface is considered dry for a given time interval $\Delta t$. If the surface temperature $T_s$ is greater than 0° C. and the $RH_{eff}$ is greater than 80%, then the surface is considered wet for the given time interval $\Delta t$. If the surface is determine to be dry for the time interval $\Delta t$, then the previous total wet time $t_{wet}$ is divided by the total previous time $t_{n-1}$ plus the current time interval $\Delta t$ to obtain the new TOW. If the surface is determined to be wet, then the previous total wet time $t_{wet}$ is added to the current time interval $\Delta t$ and then divided by the total previous time $t_{n-1}$ plus the current time interval $\Delta t$ to obtain the new TOW. The TOW is then used to establish the time of wetness category $\tau$ according to ISO 9223.

To obtain an ISO corrosivity category for a marine environment, the chloride accumulation rate ($\dot{m}^{Cl}$) is determined and combined with TOW category. The chloride deposition rate ($\dot{m}^{Cl}$) is calculated using the $RH_{eff}$, air temperature, surface temperature, solution resistance $R_s$ at each measurement time interval $\Delta t$. Also, the deliquescence relative humidity for NaCl (DRH), previously calculated chloride deposition $m^{Cl}_{n-1}$ and peak to peak noise level for the chloride mass measurement $m^{Cl}_{pp}$ are also used as inputs. If the $RH_{eff}$ is less than the DRH, then the total mass rate of chloride ($\dot{m}^{Cl}$) is simply the previous total mass of chloride $m^{tot}_{n-1}$ divide by the total previous time $t_{n-1}$ plus the time interval $\Delta t$. If the $RH_{eff}$ is greater than the DRH, and the surface temperature $t_s$ is greater than the air temperature $t_a$, then the current mass of chloride is calculated from the solution resistance $R_s$. When $RH_{eff}$ is greater than the DRH the surface is expected to be wet, and when the surface temperature $t_s$ is greater than the air temperature $t_a$ there is a less chance that a significant condensation event would be diluting the saturated salt solution on the surface. Knowing that the solution on the surface is saturated, the expected conductivity can be determine from look up tables, and knowing the conductivity, dimensions of the gold IDE FIG. 6A, and measured solution resistance $R_s$, the mass of chloride can be calculated for the current time interval $m_n^{Cl}$. If the current mass of chloride $m_n^{Cl}$ is less than the previous mass of chloride $m_{n-1}^{Cl}$, then the total mass rate of chloride ($\dot{m}^{Cl}$) is simply the previous total mass of chloride $m^{tot}_{n-1}$ divide by the total previous time $t_{n-1}$ plus the time interval $\Delta t$. If the current mass of chloride $m_n^{Cl}$ is greater than the previous mass of chloride $m_{n-1}^{Cl}$ plus the peak to peak noise level for the chloride mass measurement $m^{Cl}_{pp}$, then the mass of chloride increases by the amount given by the difference of the current mass of chloride $m_n^{Cl}$ minus the previous mass of chloride $m_{n-1}^{Cl}$. So that the total mass rate of chloride accumulation ($\dot{m}^{Cl}$) is given by difference of the current mass of chloride $m_n^{Cl}$ minus the previous mass of chloride $m_{n-1}^{Cl}$ plus the previous total mass of chloride $m^{tot}_{n-1}$ all divided by total previous time $t_{n-1}$ plus the time interval $\Delta t$. The chloride mass chloride accumulation rate ($\dot{m}^{Cl}$) is used to determine the salinity category according to ISO 9223, and then combined to obtain an atmospheric corrosivity category base on environmental parameters.

TABLE 3

Environmental classification for percent time of wetness according to ISO 9223.

| | Category | | | |
|---|---|---|---|---|
| $\tau_1$ | $\tau_2$ | $\tau_3$ | $\tau_4$ | $\tau_5$ |
| Time of wetness (%) $\tau \leq 0.1$ | $0.1 < \tau \leq 3$ | $3 < \tau \leq 30$ | $30 < \tau \leq 60$ | $60 < \tau$ |

Significant temperature differences may exist between the ambient air and the surface of a structure due to radiative heating and cooling through a diurnal cycle or temperature transitions associated with operation. The effective relative humidity ($RH_{eff}$) at a surface of a part can be determined knowing the air temperature ($T_a$), relative humidity (RH), and surface temperature ($T_s$). The relative humidity (RH) is defined as the ratio of the partial pressure of water vapor ($e_w$) in the air mixture to the saturated vapor pressure of water ($e^*_w$) at a given temperature.

$$RH = \frac{e_w}{e^*_w} \times 100\% \qquad (6)$$

The Antoine Equation can be used to estimate the saturated vapor pressure of water as a function of temperature for a temperature range of −40° C. to 50° C.

$$e^*_w = (1.0007 + 3.46 \times 10^{-6} P) \times (6.1094) e^{\left(\frac{17.625 T}{243.04 + T}\right)} \qquad (7)$$

where T is the temperature (dry bulb) in degrees Celsius, P is the absolute pressure in hectopascals. With the sensed values of air temperature and relative humidity, $e_w$ can be calculated using the above equations. Furthermore, once $e_w$ is known, the relative humidity based on the surface temperature can be determined from the resulting equation:

$$RH_{eff} = RH \times \exp\left[\frac{aT_a}{b+T_a}\right] \times \exp\left[\frac{-aT_s}{b+T_s}\right] \qquad (8)$$

where variables a and b are 17.625 and 243.04° C., respectively. An improved estimate of TOW may be achieved by using the effective relative humidity ($RH_{eff}$) to predict if a surface is wet or dry.

Finally, time of wetness can be predicted by calculating the dew point temperature ($T_d$) and comparing it to the surface temperature. When dew point is above the surface temperature, the surface is expected to be wet. This does not account for the deliquescence of hydrophilic salts and corrosion products that will hydrate at temperatures above the dew point. The dew point calculation and comparison to surface temperature is best used as a sensor test to verify proper operation of the Au IDE sensor. Specifically, when surface temperature is less than the dew point temperature, $R_s$ should be less than the upper limit of the sensor impedance.

$$T_d = \frac{b\left[\ln\left(\frac{RH}{100}\right) + \frac{aT}{b+T}\right]}{a - \ln\left(\frac{RH}{100}\right) - \frac{aT}{b+T}} \qquad (9)$$

where again variables a and b are 17.625 and 243.04° C., respectively.

The sensor suite provides measurement of air temperature, surface temperature and relative humidity. The effective relative humidity $RH_{eff}$ can be calculated using Equation 8. The ISO time of wetness as a percentage of total exposure time ($t_{n-1} + \Delta t$), and for an interval window of interest can then be determined. The TOW is determined as the time $RH_{eff}$ is greater than 80% and $T_s$ greater than 0° C. relative to total time of exposure. Using the sensor system, TOW is updated at each measurement time interval ($\Delta t$). Similarly, dew point temperature and threshold values for wetness as measured by a Au IDE sensor can also be used for estimating TOW.

According to ISO 9223, air-borne salinity is expressed as a deposition rate of a mass of chloride ions accumulated per surface area per day (mg/(m²*day)) (see Table 4 below). The solution resistance sensor is used to estimate chloride mass accumulation rate ($\dot{m}^{Cl}$). By assuming a conductivity of the moisture present on the Au IDE sensor, the mass of chloride on the sensor at a given time ($m_n^{Cl}$) can be determined from solution resistance ($R_s$), Au IDE geometry and properties of the salt solution (see Table 5 below and Equation 10) at a given time. With the best estimates being obtained using solution resistance values obtained under specific environmental conditions for the deliquescence relative humidity (DRH), surface temperature and air temperature. When the effective relative humidity reaches the deliquescence relative humidity (DRH) for NaCl (75.7%) a saturated NaCl solution (6.16 M NaCl) is formed on the sensor surface. A solution resistance or chloride mass measurement can be accepted for use in determining chloride accumulation rate, when effective RH is greater than 75.7%, and the surface temperature is higher than the air temperature. The requirement for surface temperature to be higher than air temperature is used to avoid condensing conditions. The volume of salt solution and mass of chloride per unit area ($m_n^{Cl}$) can be estimated using the dimensions of the Au IDE, and the conductivity of saturated NaCl (225 mS/cm) (Table 5, Equation 9). Under these conditions, any increase in chloride ($m_n^{Cl}$) relative to the previous time interval chloride measurement ($m_{n-1}^{Cl}$) can be treated as chloride accumulation. When the chloride mass increases relative to the previous mass measurement plus the signal noise level ($m_{p-p}^{Cl}$) it is recorded as a significant change for use in calculating the total chloride accumulation ($m^{tot}$). If the current chloride mass reading is not significant, then the chloride mass accumulation rate is simply the previous total mass ($m_{n-1}^{tot}$) divided by the previous total time ($t_{n-1}$) plus the current time interval ($\Delta t$). When the increase is significant, then the accumulation rate is calculated as the difference between the most recent chloride mass measurement ($m_n^{Cl}$) and previous mass measurement ($m_{n-1}^{Cl}$) added to the last total mass ($m_{n-1}^{tot}$) record, all divided by the previous total time ($t_{n-1}$) plus the current time interval ($\Delta t$).

TABLE 4

Environmental classification for chloride deposition rate [ISO-9223].

| | Category | | | |
|---|---|---|---|---|
| | $S_0$ | $S_1$ | $S_2$ | $S_3$ |
| Deposition rate of chloride mg/(m²-day) | S ≤ 3 | 3 < S ≤ 60 | 60 < τ ≤ 300 | 300 < τ ≤ 1500 |

TABLE 5

Parameters used to determine mass of chlorine from resistance measurements using the gold IDE. For the values given, to obtain specific mass of chloride in units of square meters. Equation 10 needs to be multiplied by $10^6$ mm²/m².

| Parameter | Symbol | Value | Notes |
|---|---|---|---|
| Au IDE gap width | w | 0.10 mm | |
| Au IDE gap length | l | 54.9 mm | |
| Au IDE gap area | A | 5.49 mm² | A = w * l |
| Concentration of saturated NaCl | $C_s^{NaCl}$ | 0.35999 mg/mm³ | |
| Weight percent Cl in NaCl | $\omega_{Cl}$ | 37.76% | 100% * $MW_{Cl}/MW_{NaCl}$ |
| Conductivity of saturated NaCl soln. | κ | 0.0225 S/mm | |
| Solution resistance | R | ohms | Measured value |
| Specific mass of Cl | $m^{Cl}$ | mg/m² | |

$$m^{Cl} = \frac{w^2 * C_{sat}^{NaCl} * \omega}{\kappa * A} * \frac{1}{R_s} \quad (10)$$

Another advantageous aspect of the technology includes sensor validation be used to detect errors and provides sensor confidence values. Sensor validation may for example be based on limit tests and analytical redundancies. Limit tests are based on the known output spans/ranges for each sensor, and expected noise levels when operating properly. When sensor output readings are outside of the sensor's normal span/range or no noise is detected, a sensor fault condition is reported. These tests can, for example, be embedded as firmware in the sensor node for automated execution of validation tests.

Significant analytic redundancies exist between the environmental and corrosion sensors. Built-in-tests can be used for error checking the effective relative humidity ($RH_{eff}$) measurements, solution conductivity, and polarization resistance as shown by the flowchart of FIG. 5. The following example rules can be executed by one or more processors at sample intervals. The fault logic is based on the assumptions for the relationships between RH, solution conductivity, and corrosion. Specifically, when the relative humidity is greater than 90%, $R_s$ and $R_p$ should be lower than their upper limit values.

Figure 10:
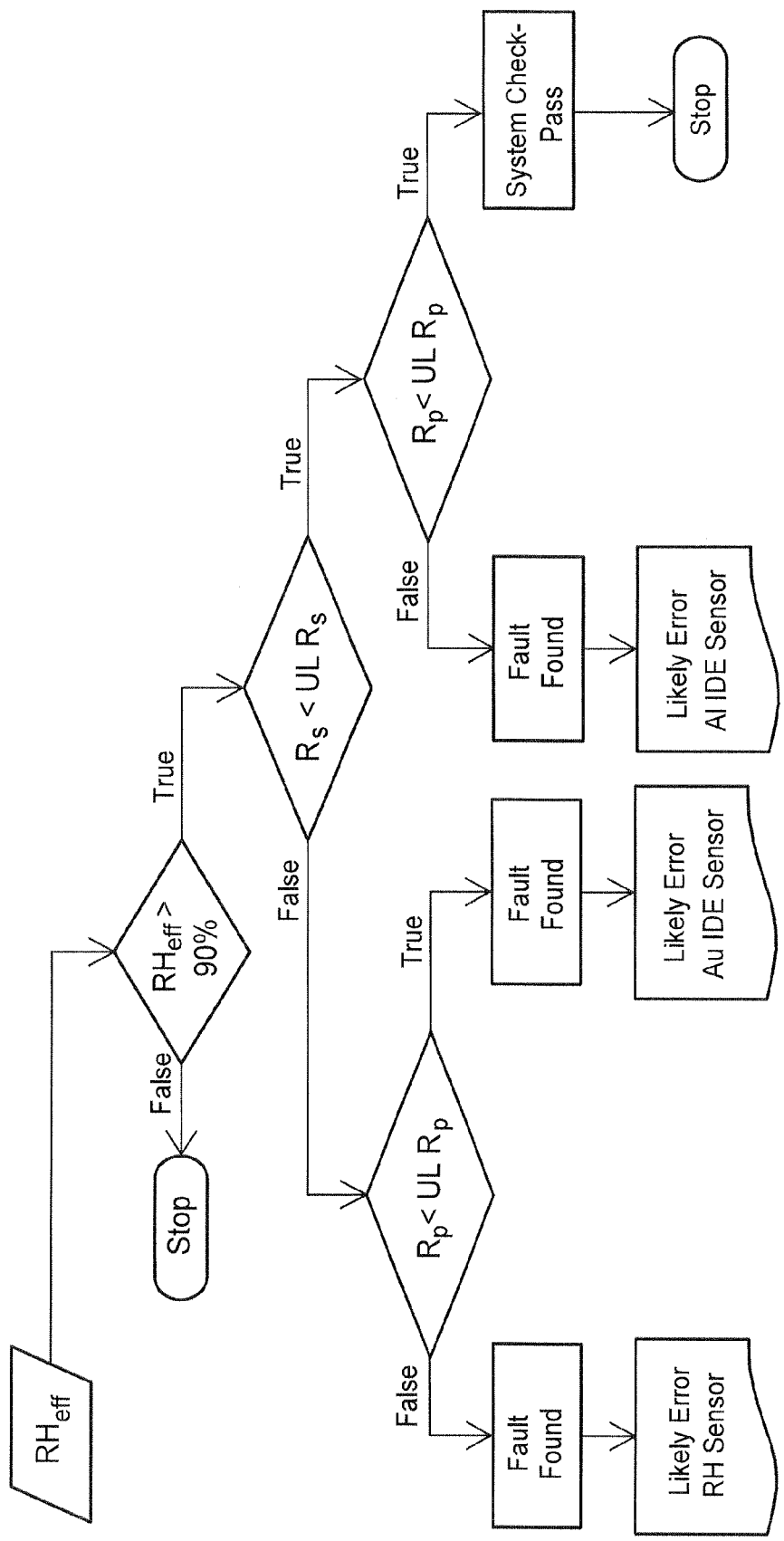
FIG. 10 is a flow chart non-limiting example procedures for determining fault conditions based on analytical redundancies between relative humidity, solution resistance (Au IDE), and corrosion rate (Al IDE) sensors.

FIG. 10 is a flow chart non-limiting example procedures for determining fault conditions based on analytical redundancies between relative humidity, solution resistance (Au IDE), and corrosion rate (Al IDE) sensors. Given that $RH_{eff}$ is greater than a threshold value, then if the solution resistance and corrosion rate sensors are working correctly, the $R_s$ measure should be lower than the sensors upper limit UL $R_s$, and the $R_p$ sensor should be less than the sensors upper limit UL $R_p$. If these conditions are satisfied, then the system passes the system check. An alert signal may be generated to indicate a humidity sensor fault if the measured relative humidity is above first threshold value of 90%, and the measured $R_s$ sensor is below the upper limit UL $R_s$, and the measured $R_p$ is less than the sensors upper limit UL $R_p$ value. Moreover, an alert signal may be generated indicating a corrosion rate $R_p$ sensor fault if the measured Rp is not below the upper limit UL $R_p$ threshold when the measured $RH_{eff}$ exceeds the 90% threshold, and the $R_s$ parameter is below the upper limit UL $R_s$ parameter. Moreover, an alert signal may be generated indicating a solution resistance $R_s$ sensor fault if the measured Rs is not below the upper limit UL $R_s$ threshold when the measured $RH_{eff}$ exceeds the 90% threshold, and the corrosion rate $R_p$ parameter is below the upper limit UL $R_p$ parameter.

Non-Limiting Example

A corrosion sensor node SN was used for continuous monitoring of the interior of a ground vehicle for 39 days. The sensor node contained a suite of sensors including air temperature and relative humidity (Sensirion SHT7x series) and surface temperature (standard thin film platinum RTD from US Sensor Corp), Au IDE (Standard ER Micro Sensor) and aluminum alloy IDE (MiniFAB Ltd). The sensors were packaged in a small sensor node that can wirelessly transfer data. The wireless interface employed was a Meshnetics ZigBit Zigbee communications module. The system was configured to sample the transducers every 10 minutes and store the data. Periodically, the data were wirelessly downloaded by a user to a laptop computer.

The data retrieved from the sensor node SN was given as an array with date and time stamps. The data array from the sensor node included air and surface temperature in degrees Celsius, percent relative humidity, and solution resistance and polarization resistances in units of ohms. Once downloaded, the data were processed to obtain corrosion rates, cumulative corrosion and ISO corrosivity categories based on the environmental data and corrosion rate data. This processing may also be accomplished locally at the sensor node SN as described above.

Figure 11:
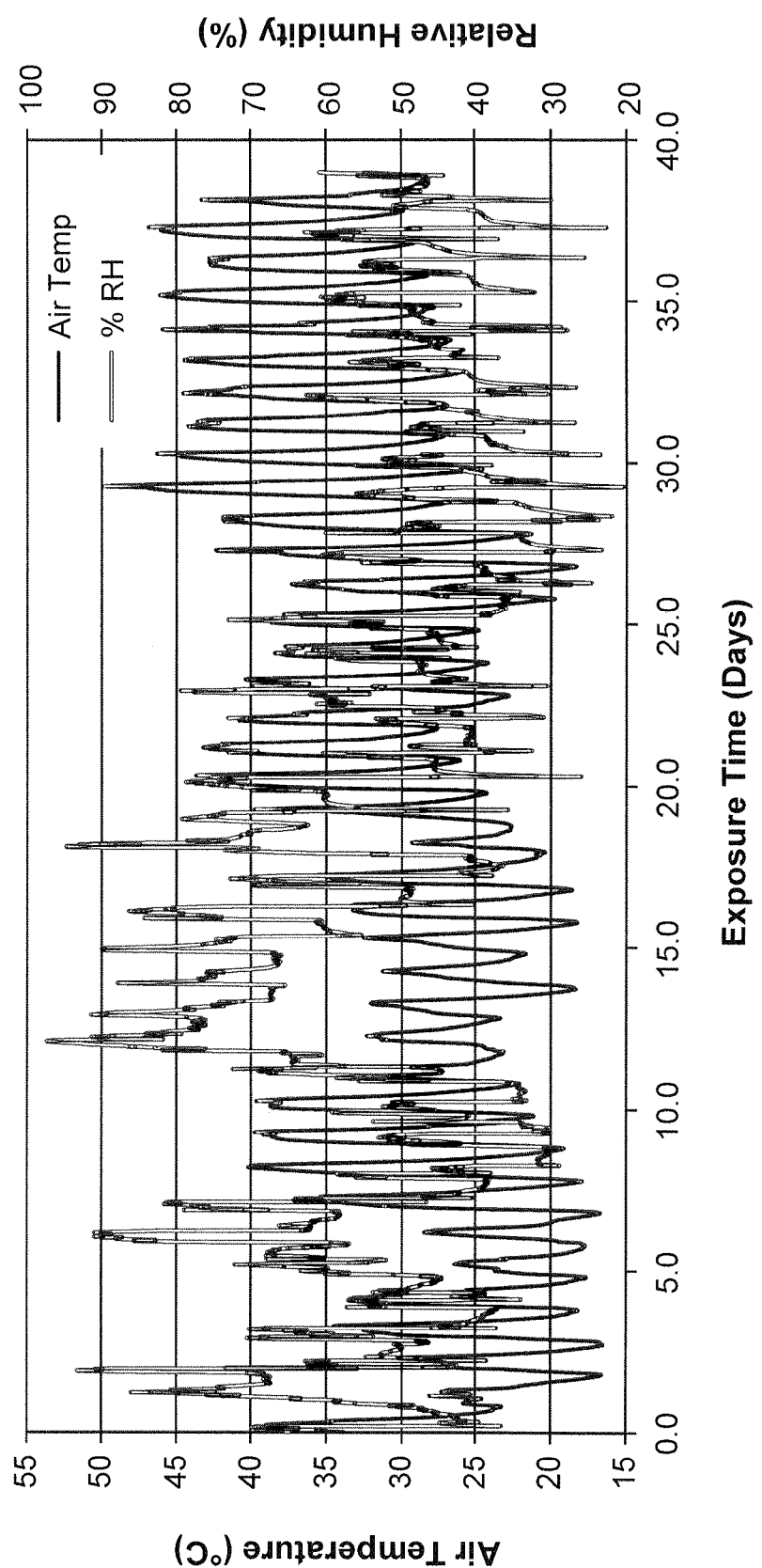
FIG. 11 is a graph of air temperature and relative humidity measurements for the interior space of a ground vehicle obtained according to a non-limiting example.

FIG. 11 is a graph of air temperature and relative humidity measurements for the interior space of a ground vehicle obtained according to a non-limiting example. The graph shows an expected inverse correlation between air temperature and relative humidity.

Figure 12:
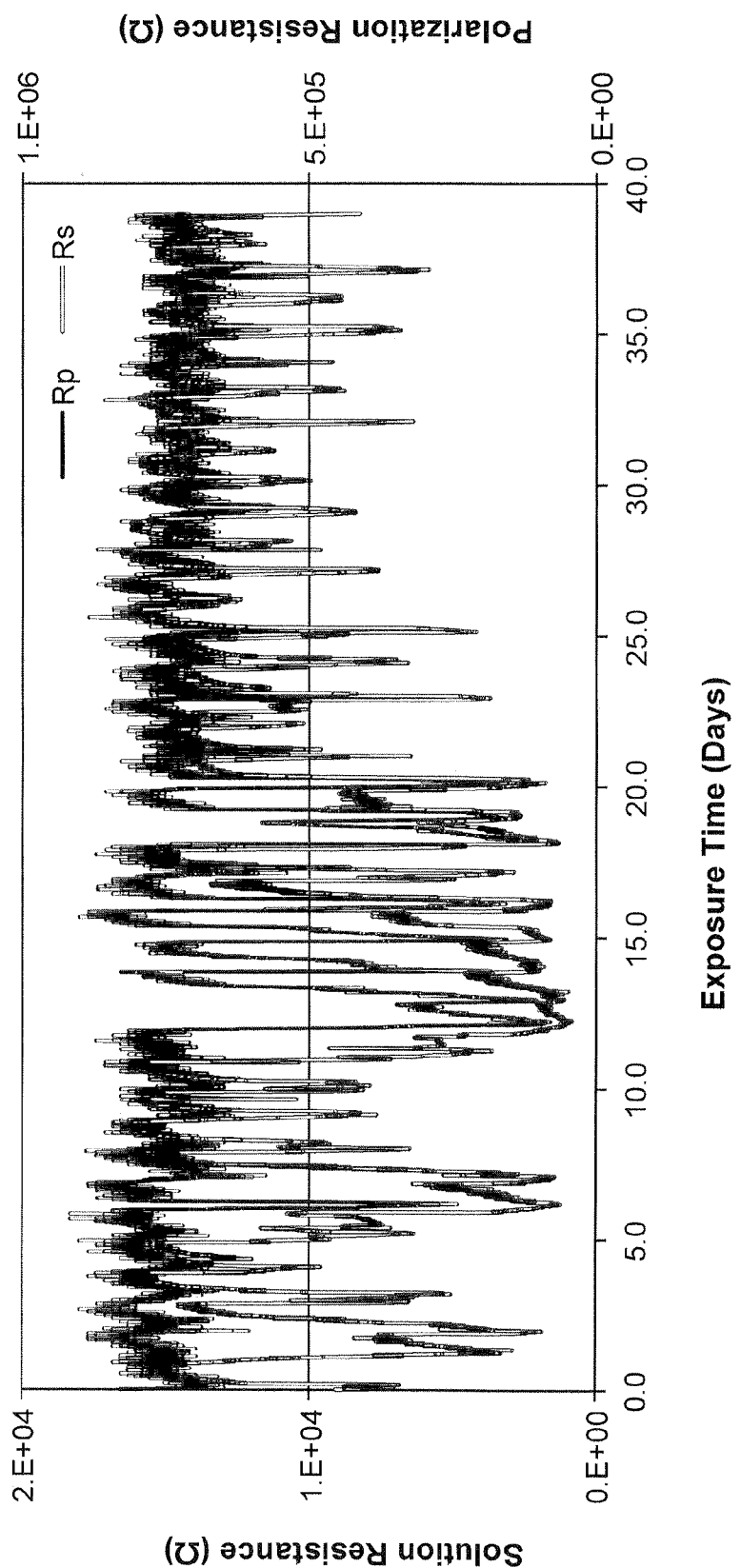
FIG. 12 is a graph of solution and polarization resistance measurements for the interior space of a ground vehicle obtained according to a non-limiting example.

FIG. 12 is a graph of solution and polarization resistance measurements for the interior space of a ground vehicle obtained according to a non-limiting example. Solution resistance and polarization resistance have similar time responses to environmental conditions.

Figure 13:
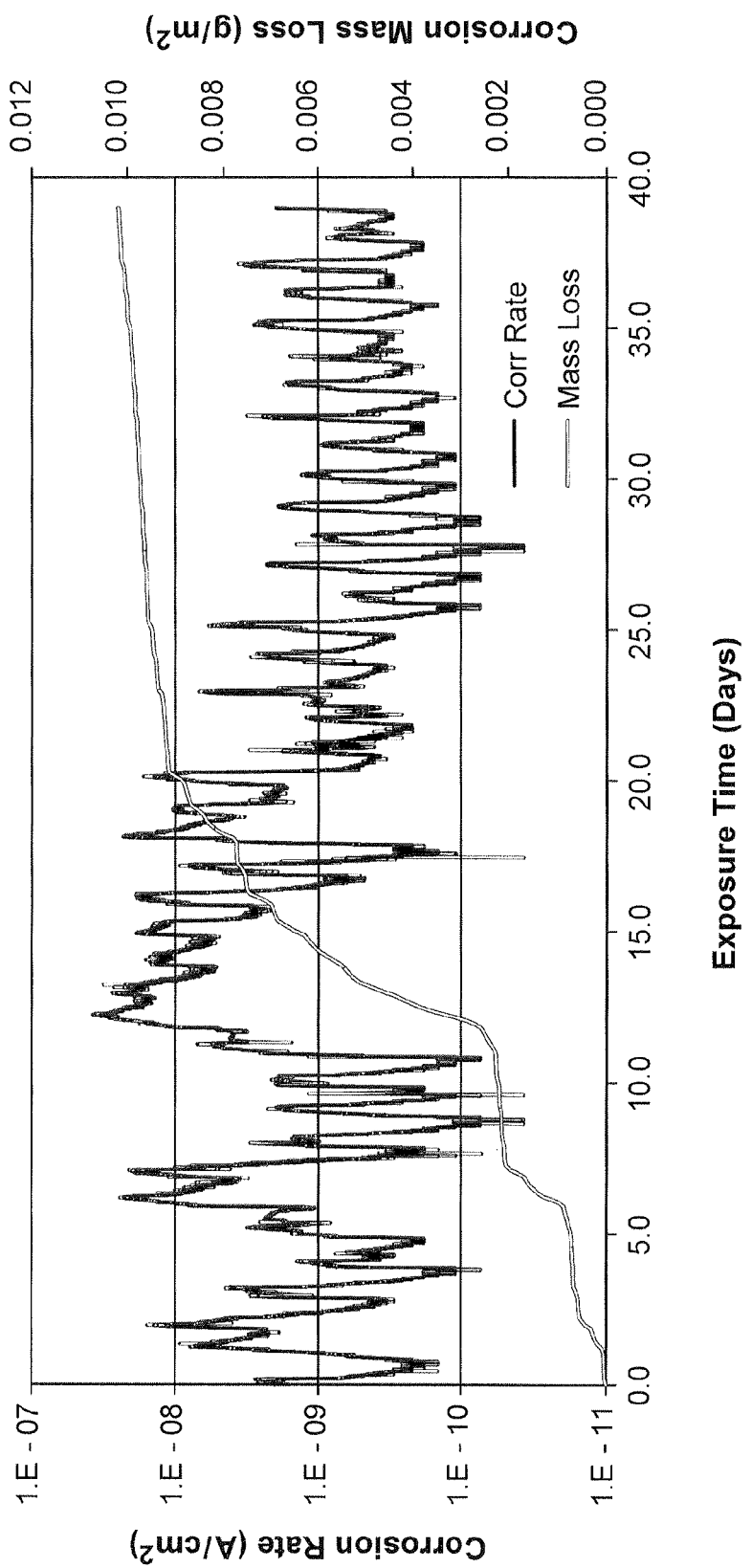
FIG. 13 is a graph of corrosion rate and total cumulative mass loss for aluminum alloy sensor in the interior space of a ground vehicle obtained according to a non-limiting example.

FIG. 13 is a graph of corrosion rate and total cumulative mass loss for aluminum alloy sensor in the interior space of a ground vehicle obtained according to a non-limiting example.

Figure 14:
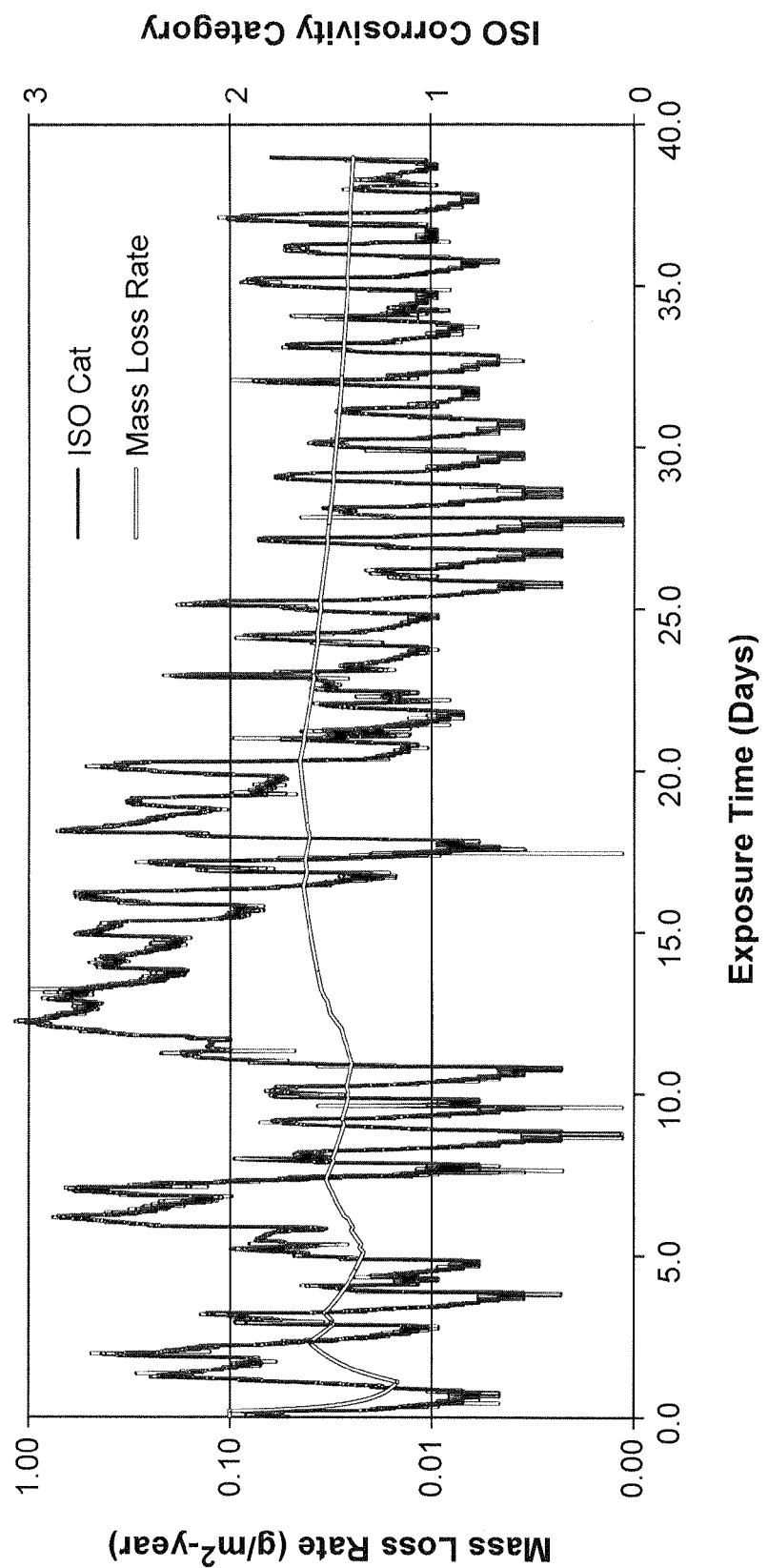
FIG. 14 is a graph of the annualized mass loss rate and ISO corrosivity category for aluminum alloy sensor in the interior space of a ground vehicle obtained according to a non-limiting example.

FIG. 14 is a graph of the annualized mass loss rate and ISO corrosivity category for aluminum alloy sensor in the interior space of a ground vehicle obtained according to a non-limiting example. Mass loss rate has significant variation associated with diurnal cycles, while the ISO category is a more stable measure of longer term atmospheric corrosivity.

The technology described above uses multimodal measurements of environment to obtain reliable measurements of atmospheric corrosivity base on separate environmental and corrosion rate methods. These redundant methods improve confidence in the corrosivity classification and support automated sensor validation to identify fault conditions. The low power sensor network is flexible and reconfigurable to support instrumentation of the broadest possible range of structures. The system is compact and can be fit into difficult to access areas, and can run for prolonged periods using either batteries of energy scavenging devices. The flexible modular network interface is compatible with existing network system within industrial plants or transportation monitoring systems such as health usage monitoring systems for aircraft. The sensors allow for determination of unique conditions that control corrosion such as the surface effective relative humidity and salt accumulation rate. These unique environment parameters are complimented by corrosion rate sensors that can be fabricated from alloys use in the structure, and alloy combinations representative of the galvanic couples within the structure. Eddy current sensors for measurements of cumulative damage permits verification of the corrosion rate data over long periods.

Although various embodiments have been shown and described in detail, the claims are not limited to any particular embodiment or example. None of the above description should be read as implying that any particular member, step, range, or function is essential such that it must be included in the claims scope. The scope of patented subject matter is defined only by the claims. The extent of legal protection is defined by the words recited in the allowed claims and their equivalents. All structural and functional equivalents to the members of the above-described preferred embodiment that are known to those of ordinary skill in the art are expressly incorporated herein by reference and are intended to be encompassed by the present claims. Moreover, it is not necessary for a device or method to address each and every problem sought to be solved by the technology described, for it to be encompassed by the present claims. No claim is intended to invoke paragraph 6 of 35 USC §112 unless the words "means for" or "step for" are used. Furthermore, no embodiment, feature, component, or step in this specification is intended to be dedicated to the public regardless of whether the embodiment, feature, component, or step is recited in the claims.

The invention claimed is:

1. A method of determining corrosivity associated with a location near, on, or within a structure exposed to an environment that can corrode the structure, where a sensor node is mounted at the location, the sensor node performing steps comprising:
   measuring environmental sensor information using one or more environmental sensors and corrosion sensor information using one or more corrosion sensors, where the environmental sensor information includes one or more of measured relative humidity, air temperature, surface temperature and conductivity parameters, and the corrosion sensor information includes a corrosion rate parameter;
   processing, by a data processor, the environmental sensor information to obtain for the sensing node a first atmospheric corrosivity category value in accordance with a corrosivity classification system;
   processing, by the data processor, the corrosion sensor information to obtain a second atmospheric corrosivity category value for the sensing node in accordance with the corrosivity classification system; and
   providing one or more of the first and second atmospheric corrosivity category values for use in determining a corrosion classification value for the location.

2. The method in claim 1, wherein one of the corrosion sensors includes electrodes made of the same metal, and wherein the corrosion rate parameter is determined from a current measured between the metal electrodes.

3. The method in claim 1, wherein one of the corrosion sensors includes dissimilar metals, and wherein the corrosion rate parameter is determined from a galvanic current measured between the dissimilar metals.

4. The method in claim 1, wherein one of the corrosion sensors uses an eddy current induction sensor for measuring a total mass loss of a metal sample, and wherein the corrosion rate parameter is determined from the measured total mass loss of the metal sample and a time of exposure.

5. The method in claim 1, further comprising determining a chloride mass using conductivity measurements associated with the sensing node.

6. The method in claim 5, wherein the chloride mass is determined only when a relative humidity detected at the sensor node is above 70%.

7. The method in claim 5, further comprising determining a chloride deposition rate.

8. The method in claim 1, further comprising using measured relative humidity, air temperature, and surface temperature to adjust the relative humidity based on the surface temperature of the structure.

9. The method in claim 1, further comprising determining a time of wetness associated with the sensing node.

10. The method in claim 9, wherein time of wetness is determined based on an amount of time that the measured relative humidity exceeds a threshold value, or an amount of time that the measured conductivity exceeds a threshold value.

11. The method in claim 1, further comprising determining a corrosivity measurement error value or a corrosivity measurement confidence value using the environmental and the corrosion sensor information.

12. The method in claim 11, further comprising generating an alert signal if the corrosivity measurement error value exceeds an error threshold or the corrosivity measurement confidence value is less than a confidence threshold.

13. The method in claim 1, further comprising generating an alert signal indicating a humidity sensor fault if the measured relative humidity is below a first threshold, the measured conductivity sensor exceeds a second threshold, and the corrosion rate parameter exceeds a third threshold.

14. The method in claim 1, further comprising generating an alert signal indicating a conductivity sensor fault if the measured conductivity is below a first threshold, the measured relative humidity exceeds a second threshold, and the corrosion rate parameter exceeds a third threshold.

15. The method in claim 1, further comprising generating an alert signal indicating a corrosion rate parameter fault if the measured corrosion rate is below a first threshold, the measured relative humidity exceeds a second threshold, and the conductivity sensor parameter exceeds a third threshold.

16. The method in claim 1, wherein the corrosivity classification system is based on an ISO 9223 corrosivity of atmospheres classification system.

17. The method in claim 1, wherein the providing step includes sending information regarding one or both of the first and second atmospheric corrosivity categories to one or more other nodes.

18. The method of claim 1, wherein the sensing node communicates with the one or more other nodes via a wired interface or a wireless interface.

19. A sensor node for measuring corrosivity associated with a location near, on, or within a structure exposed to an environment that can corrode the structure, where a sensor node is mountable at the location, the sensor node comprising:
 one or more environmental sensors configured to provide environmental sensor information including one or more of measured relative humidity, air temperature, surface temperature and conductivity parameters;
 one or more corrosion sensors configured to provide corrosion sensor information including a corrosion rate parameter;
 a data processor configured to process:
  the environmental sensor information to obtain for the sensing node a first atmospheric corrosivity category value in accordance with a corrosivity classification system, and
  the corrosion sensor information to obtain a second atmospheric corrosivity category value for the sensing node in accordance with the corrosivity classification system; and
 a communications interface configured to provide one or more of the first and second atmospheric corrosivity category values for use in determining a corrosion classification value for the location.

20. The sensor node in claim 19, wherein the one or more environmental sensors include air temperature, surface temperature, and conductivity sensors, and wherein the one or more corrosion sensors include a corrosion sensor with two identical metal electrodes and a corrosion sensor made of dissimilar metals.

21. The sensor node in claim 19, wherein the one or more environmental sensors include an electrode sensor including two noble metal electrodes for estimating time of wetness and conductivity.

22. The sensor node in claim 21, wherein the electrode sensor includes two interdigitated gold electrodes.

23. The sensor node in claim 19, wherein the one or more environmental sensors include a conductivity sensor configured to be excited with a DC voltage or an AC voltage to obtain a conductivity measurement.

24. The sensor node in claim 19, wherein the one or more corrosion rate sensors include an electrode sensor composed of two electrodes of similar metal or alloy to estimate the corrosion rate.

25. The sensor node in claim 24, wherein the electrode sensor configured to be excited with a DC voltage or an AC voltage to obtain a corrosion rate measurement.

26. The sensor node in claim 19, wherein the one or more corrosion rate sensors include an electrode sensor composed of two electrodes of dissimilar metal or alloy to estimate corrosion rate.

27. The sensor node in claim 26, wherein the electrode sensor includes a zero resistance ammeter that measures galvanic current.

28. The sensor node in claim 19, wherein the one or more corrosion sensors include an induction coil for making eddy current measurements of an alloy sample.

29. A controller node for determining corrosivity associated with a structure exposed to an environment that can corrode the structure, the controller node comprising:
 a communications interface configured to receive from each of multiple sensing nodes associated with a corresponding location near, on, or within the structure measured environmental sensor information and measured corrosion sensor information, where the environmental sensor information includes one or more of measured relative humidity, air temperature, surface temperature and conductivity parameters, and the corrosion sensor information includes a corrosion rate parameter;
 a data processor configured to process:
  the environmental sensor information to obtain for each of the sensing nodes a first atmospheric corrosivity category value in accordance with a corrosivity classification system, and
  the corrosion sensor information to obtain a second atmospheric corrosivity category value for each of the sensing nodes in accordance with the corrosivity classification system; and
 provide one or more of the first and second atmospheric corrosivity category values for each of the sensing nodes for use in determining a corrosion value for the sensing node's corresponding location.

30. The controller node in claim 29, wherein the data processor is configured to determine a mass loss rate associated with each sensing node.

31. The controller node in claim 29, wherein the data processor is configured to determine a chloride concentration associated with each sensing node.

32. The controller node in claim 29, wherein the data processor is configured to determine a time of wetness associated with each sensing node.

33. The controller node in claim 29, wherein the data processor is configured to determine an error parameter associated with each of the sensing nodes that provides a confidence value associated with the determined corrosivity from that sensing node.

34. The controller node in claim 29, wherein the data processor is configured to determine the error parameter for each of the sensing nodes based on a comparison between the environmental sensor information and the corrosion sensor information received for that node.

* * * * *